(12) United States Patent
Khera et al.

(10) Patent No.: US 7,237,552 B2
(45) Date of Patent: Jul. 3, 2007

(54) INSERTION/DEPLOYMENT CATHETER SYSTEM FOR INTRAFALLOPIAN CONTRACEPTION

(75) Inventors: Ashish Khera, San Francisco, CA (US); Don Gurskis, Redwood City, CA (US); Dai Ton That, Milpitas, CA (US); Betsy Swann, Newark, CA (US); Steven Bacich, Half Moon Bay, CA (US)

(73) Assignee: Conceptus, Inc., Mountain View, CA (US)

( * ) Notice: Subject to any disclaimer, the term of this patent is extended or adjusted under 35 U.S.C. 154(b) by 65 days.

(21) Appl. No.: 10/892,607

(22) Filed: Jul. 15, 2004

(65) Prior Publication Data

US 2005/0045184 A1 Mar. 3, 2005

Related U.S. Application Data

(63) Continuation of application No. 09/644,277, filed on Aug. 22, 2000, now Pat. No. 6,763,833.

(60) Provisional application No. 60/150,521, filed on Aug. 23, 1999.

(51) Int. Cl.
*A61F 6/06* (2006.01)

(52) U.S. Cl. .................... 128/830; 128/831

(58) Field of Classification Search ......... 128/830–841
See application file for complete search history.

(56) References Cited

U.S. PATENT DOCUMENTS

| 3,561,438 A | 2/1971 | Canel |
| 3,687,129 A | 8/1972 | Nuwayser |
| 3,774,600 A | 11/1973 | Cognat |
| 3,805,767 A | 4/1974 | Erb |
| 3,858,571 A * | 1/1975 | Rudolph ............... 128/831 |
| 3,858,586 A * | 1/1975 | Lessen ................. 606/49 |
| 3,973,560 A | 8/1976 | Emmett |
| RE29,345 E * | 8/1977 | Erb ..................... 128/831 |
| 4,057,063 A | 11/1977 | Gieles et al. |
| 4,111,196 A | 9/1978 | Emmett |
| 4,185,618 A | 1/1980 | Corey |
| 4,246,896 A | 1/1981 | Horne, Jr. et al. |

(Continued)

FOREIGN PATENT DOCUMENTS

CN 1047447 A 5/1990

(Continued)

OTHER PUBLICATIONS

Erb, R.A. et al., "Hysteroscopic Oviductal Blocking with Formed-in-Place Silicone Rubber Plugs," *The Journal of Reproductive Medicine*, pp. 65-68, Aug. 1979.

(Continued)

*Primary Examiner*—Michael A. Brown
(74) *Attorney, Agent, or Firm*—Blakely, Sokoloff, Taylor & Zafman LLP

(57) ABSTRACT

Contraceptive methods, systems, and devices generally improve the ease, speed, and reliability with which a contraceptive device can be deployed transcervically into an ostium of a fallopian tube. A distal portion of the contraceptive device can function as a guidewire. The proximal portion may remain in a small profile configuration while a sheath is withdrawn proximally, and is thereafter expanded to a large profile configuration engaging the surrounding tissues.

11 Claims, 21 Drawing Sheets

U.S. PATENT DOCUMENTS

| | | | |
|---|---|---|---|
| 4,353,363 A | 10/1982 | Sopeña Quesada | |
| 4,365,621 A | 12/1982 | Brundin | |
| 4,416,660 A | 11/1983 | Dafoe | |
| 4,509,504 A | 4/1985 | Brundin | |
| 4,579,110 A | 4/1986 | Hamou | |
| 4,595,000 A | 6/1986 | Hamou | |
| 4,606,336 A * | 8/1986 | Zeluff | 128/831 |
| 4,612,924 A | 9/1986 | Cimber | |
| 4,628,924 A | 12/1986 | Cimber | |
| 4,638,803 A | 1/1987 | Rand | |
| 4,700,701 A | 10/1987 | Montaldi | |
| 4,727,866 A | 3/1988 | Livesay et al. | |
| 4,788,966 A | 12/1988 | Yoon | |
| 4,932,421 A | 6/1990 | Kaali et al. | |
| 4,994,069 A | 2/1991 | Ritchart et al. | |
| 5,065,751 A | 11/1991 | Wolf | |
| 5,095,917 A | 3/1992 | Vancaillie | |
| 5,176,692 A | 1/1993 | Wilk et al. | |
| 5,207,684 A | 5/1993 | Nobles | |
| 5,226,911 A | 7/1993 | Chee et al. | |
| 5,234,437 A | 8/1993 | Sepetka | |
| 5,244,096 A * | 9/1993 | Stoner | 206/581 |
| 5,250,071 A | 10/1993 | Palermo | |
| 5,261,916 A | 11/1993 | Engelson | |
| 5,304,194 A | 4/1994 | Chee et al. | |
| 5,304,195 A | 4/1994 | Twyford, Jr. et al. | |
| 5,312,415 A | 5/1994 | Palermo | |
| 5,354,295 A | 10/1994 | Guglielmi et al. | |
| 5,354,309 A | 10/1994 | Schnepp-Pesch et al. | |
| 5,382,259 A | 1/1995 | Phelps et al. | |
| 5,458,636 A | 10/1995 | Brancato | |
| 5,474,089 A | 12/1995 | Waynant | |
| 5,499,995 A | 3/1996 | Teirstein | |
| 5,514,176 A | 5/1996 | Bosley, Jr. | |
| 5,522,822 A | 6/1996 | Phelps et al. | |
| 5,556,396 A | 9/1996 | Cohen et al. | |
| 5,562,641 A | 10/1996 | Flomenblit et al. | |
| 5,582,619 A | 12/1996 | Ken | |
| 5,601,600 A | 2/1997 | Ton | |
| 5,755,773 A | 5/1998 | Evans et al. | |
| 5,843,158 A | 12/1998 | Lenker et al. | |
| 5,935,137 A * | 8/1999 | Saadat | 128/831 |
| 6,096,052 A | 8/2000 | Callister et al. | |
| 6,143,007 A * | 11/2000 | Mariant | 606/151 |
| 6,145,505 A | 11/2000 | Nikolchev et al. | |
| 6,176,240 B1 | 1/2001 | Nikolchev et al. | |
| 6,432,116 B1 | 8/2002 | Callister et al. | |
| 6,526,979 B1 | 3/2003 | Nikolchev et al. | |
| 6,585,663 B1 * | 7/2003 | Coley | 600/551 |
| 6,634,361 B1 * | 10/2003 | Nikolchev | 128/830 |

FOREIGN PATENT DOCUMENTS

| | | |
|---|---|---|
| DE | 28 03 685 A1 | 8/1979 |
| EP | 0 010 812 A1 | 5/1980 |
| EP | 0 891 757 A2 | 10/1999 |
| GB | 2 038 186 | 7/1980 |
| GB | 2 221 095 | 6/1989 |
| NL | 7810696 | 4/1990 |
| WO | WO 93/06884 | 4/1993 |
| WO | WO 94/06503 | 3/1994 |
| WO | WO 94/10936 | 5/1994 |
| WO | WO 94/11051 | 5/1994 |
| WO | WO 96/40023 A1 | 12/1996 |
| WO | WO 96/40024 A1 | 12/1996 |
| WO | WO 97/08997 A1 | 3/1997 |
| WO | WO 98/26737 | 6/1998 |
| WO | WO 98/26737 A1 | 6/1998 |
| WO | WO 98/55046 | 12/1998 |
| WO | WO 99/15116 A1 | 4/1999 |
| WO | WO 00/13624 A1 | 3/2000 |

OTHER PUBLICATIONS

Gordon, A.G., et al., *Atlas of Gynecologic Endoscopy*, Mosby-Wolfe Press, 2nd Edition, 1995 (Title Page and Table of Contents are enclosed herewith).

Gupta, D.N. et al., "Antifertility Effect of an Intrafallopian Tubal Copper Device," *Indian J. Exp. Biol.*, vol. 14, pp. 316-319, May. 1976.

Hamou, J. et al., "Hysteroscopic Reversible Tubal Sterilization," *ACTA Europaea Fertilitatis*, vol. 15, No. 2, 1984.

Reed, T.P. et al., "Tubal Occlusion with Silicon Rubber," *The Journal of Reproductive Medicine*, pp. 25-28, Jul. 1980.

Ross, P.L. et al., "Transcatheter Tubal Sterilization in Rabbits," *Investigative Radiology*, vol. 29, No. 5, pp. 570-573, 1994.

Sciarra, J.J., et al., eds., *Advances in Female Sterilization Techniques*, Harper & Row, Publishers, 1976, Title Page and Table of Contents are enclosed herewith, pp. 169-181, 186-189.

Steptoe, P.C., "The Potential Use of Intratubal Stents for Reversible Sterilization," *Laaroscopy*, pp. 91-99, circa 1976.

Brueschke, E.E., et al., "Transcervical tubal occlusion with a steerable hysteroscope: Implantation of devices into extirpated human uteri," *Am. J. Obstet. Gynecol.*, vol. 127, No. 2, pp. 118-124, 1977.

Brundin, J., "Transcervical sterilization in the human female by ysteroscopic application of hydrogelic occlusive devices into the intramural parts of the Fallopian tubes: 10 years experience of the P-block," *European Journal of Obstetrics & Gynecology and Reporductive Biology*, vol. 39, pp. 41-49, 1991.

Complete Chinese-to-English translation of Chinese Patent Publication No. CN 1047447A.

Conceptus Annual Report (1995) pp. 3,5,7,9,13-14, and 22.

Conceptus Annual Report (1996) pp. x,3,9,and 13-14.

* cited by examiner

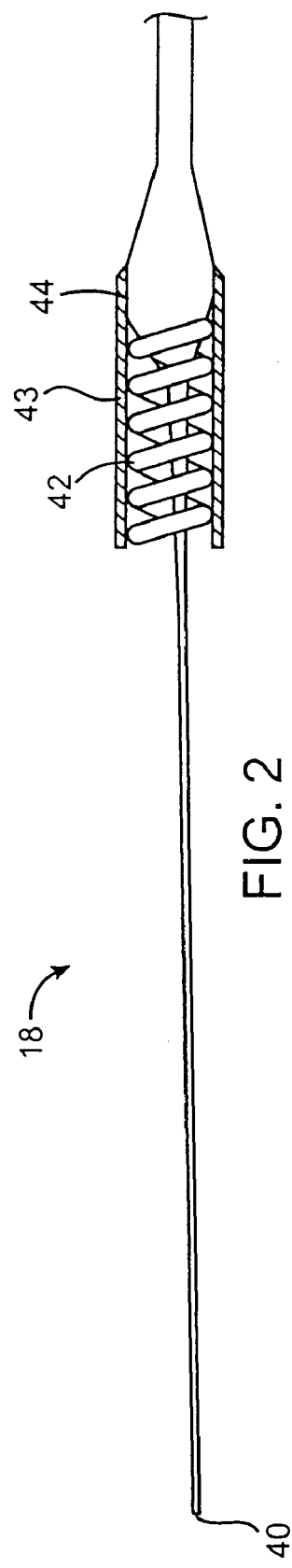
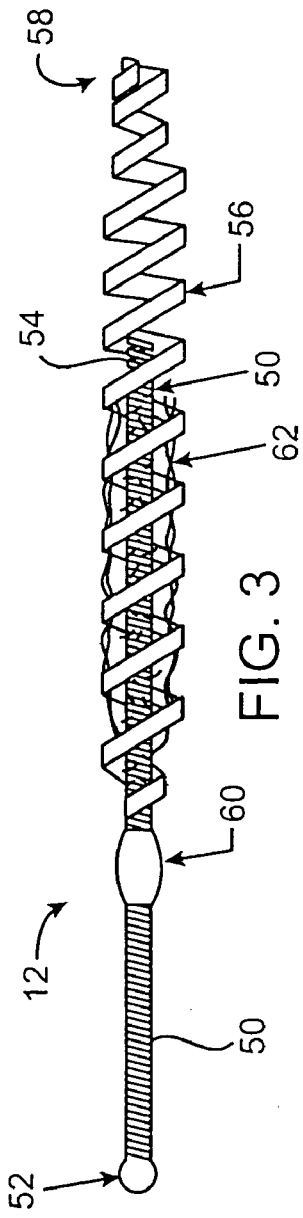
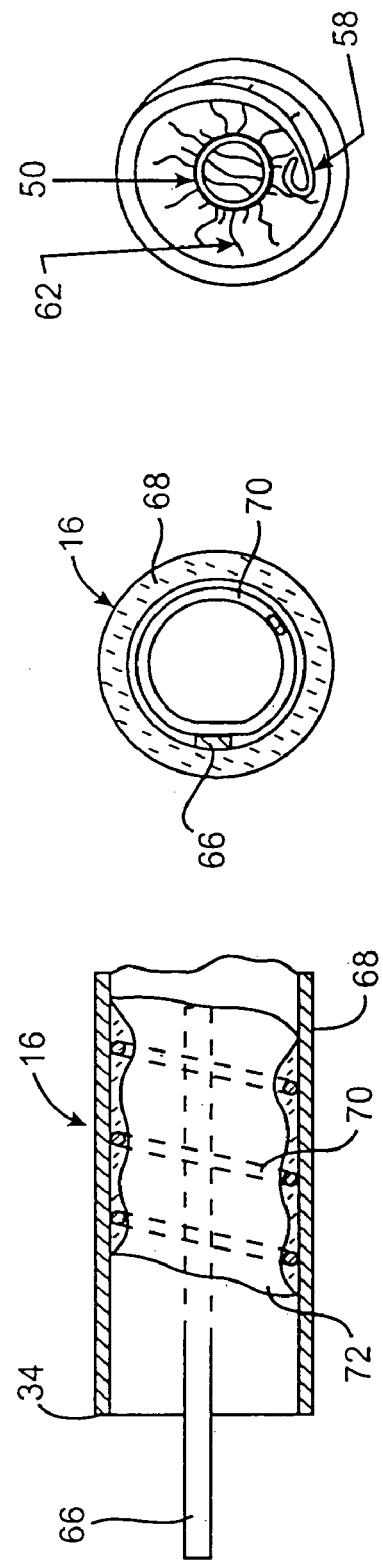
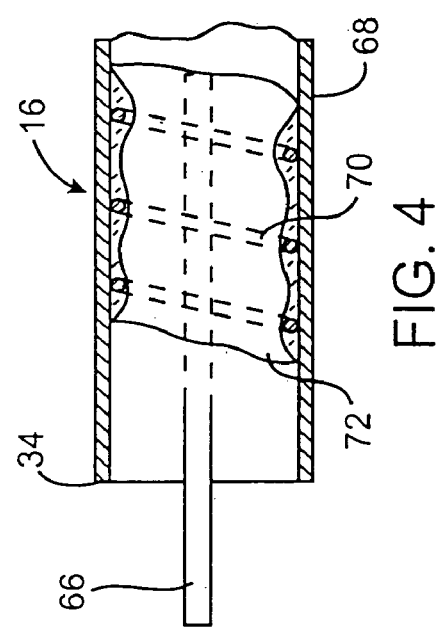
FIG. 2
FIG. 3
FIG. 3A
FIG. 4A
FIG. 4

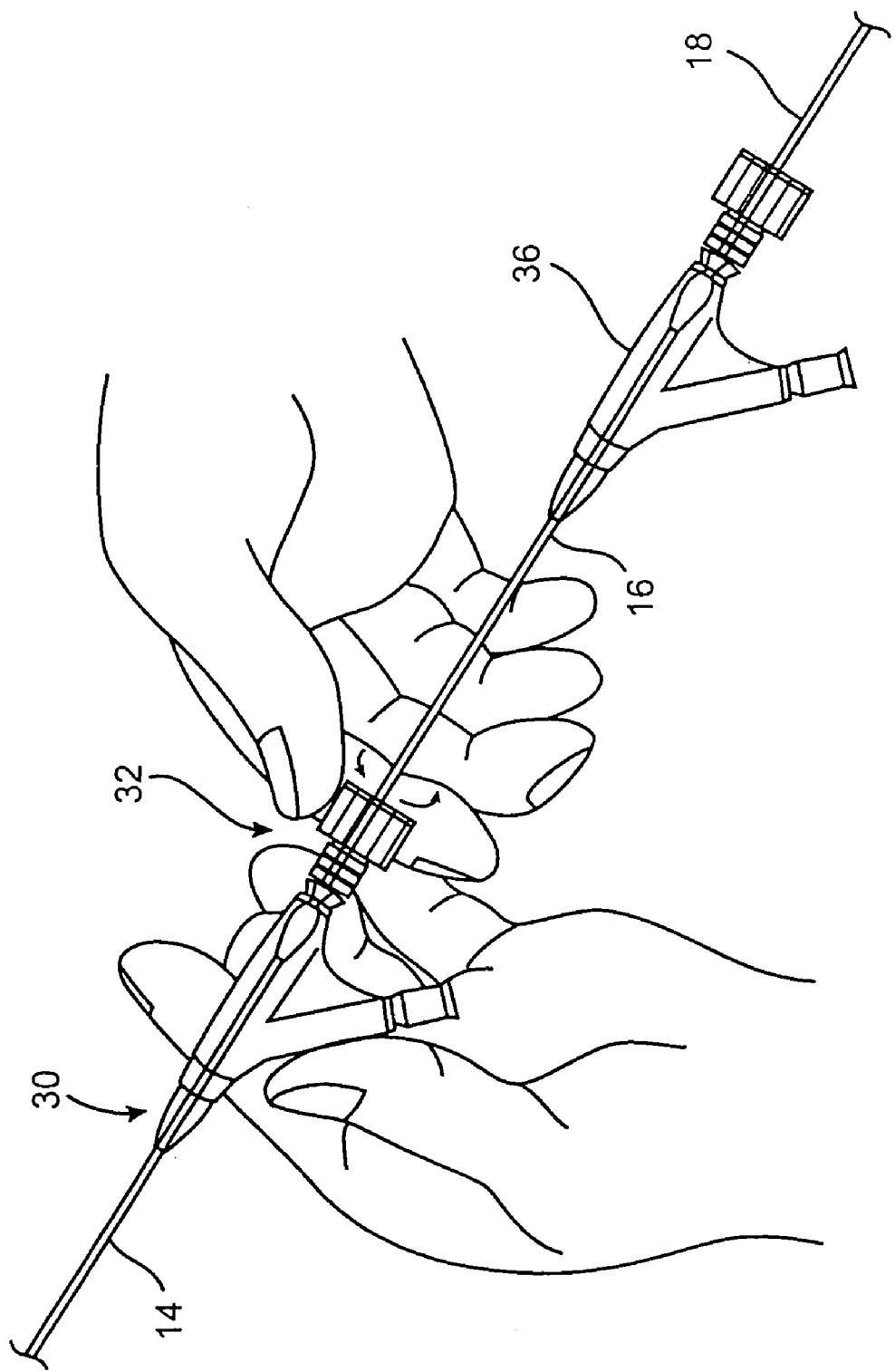
FIG. 8A1

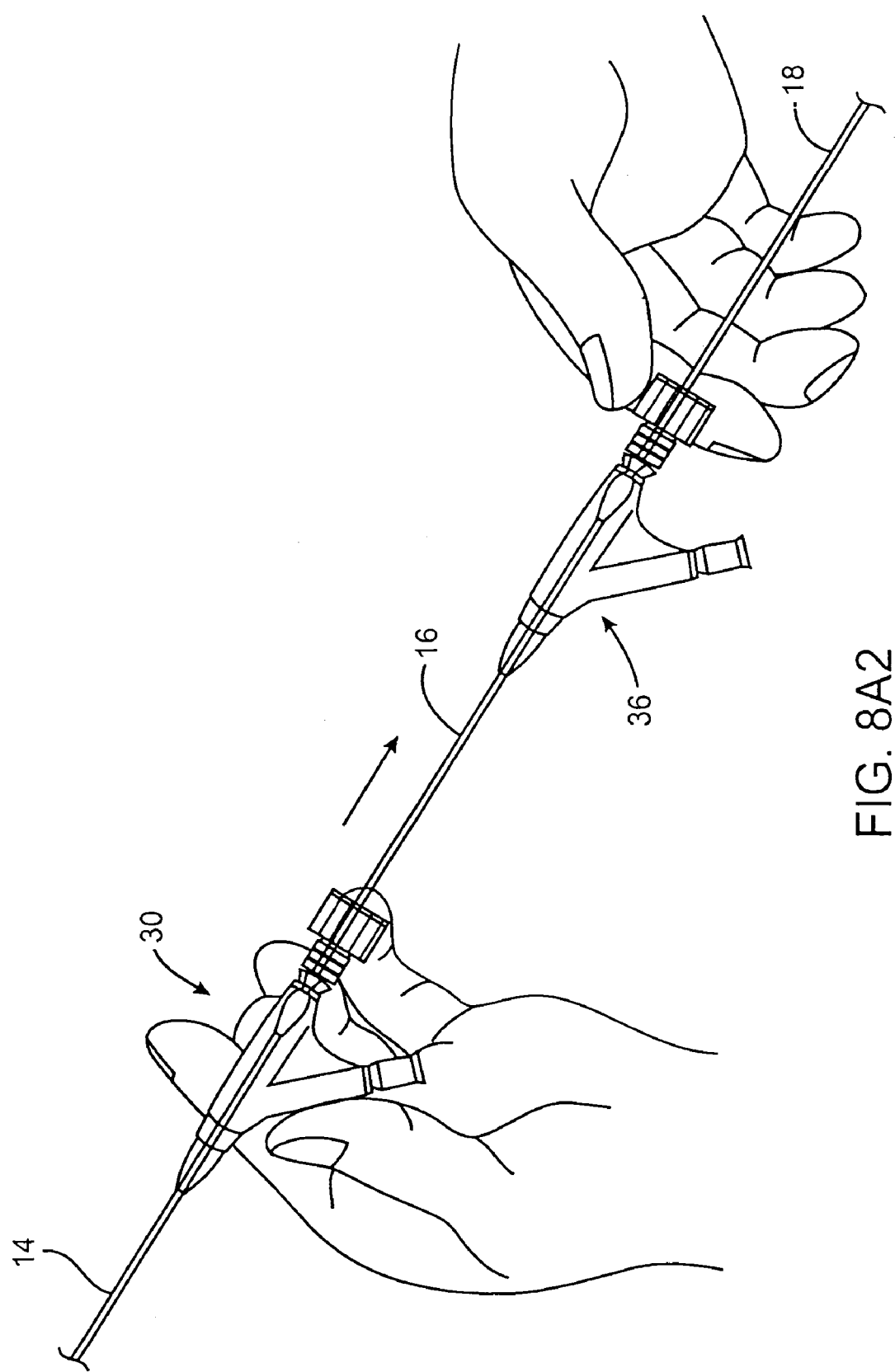
FIG. 8A2

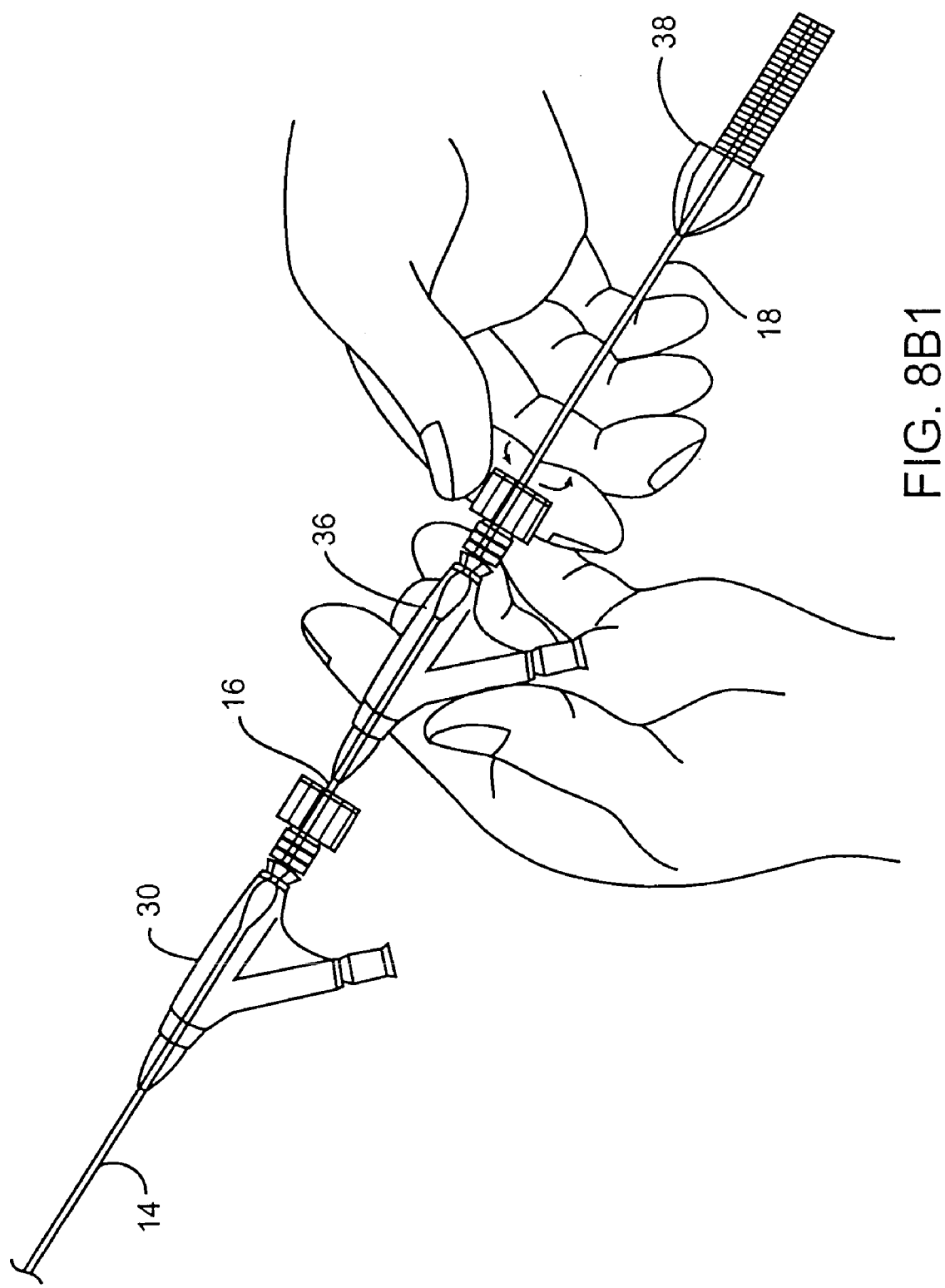
FIG. 8B1

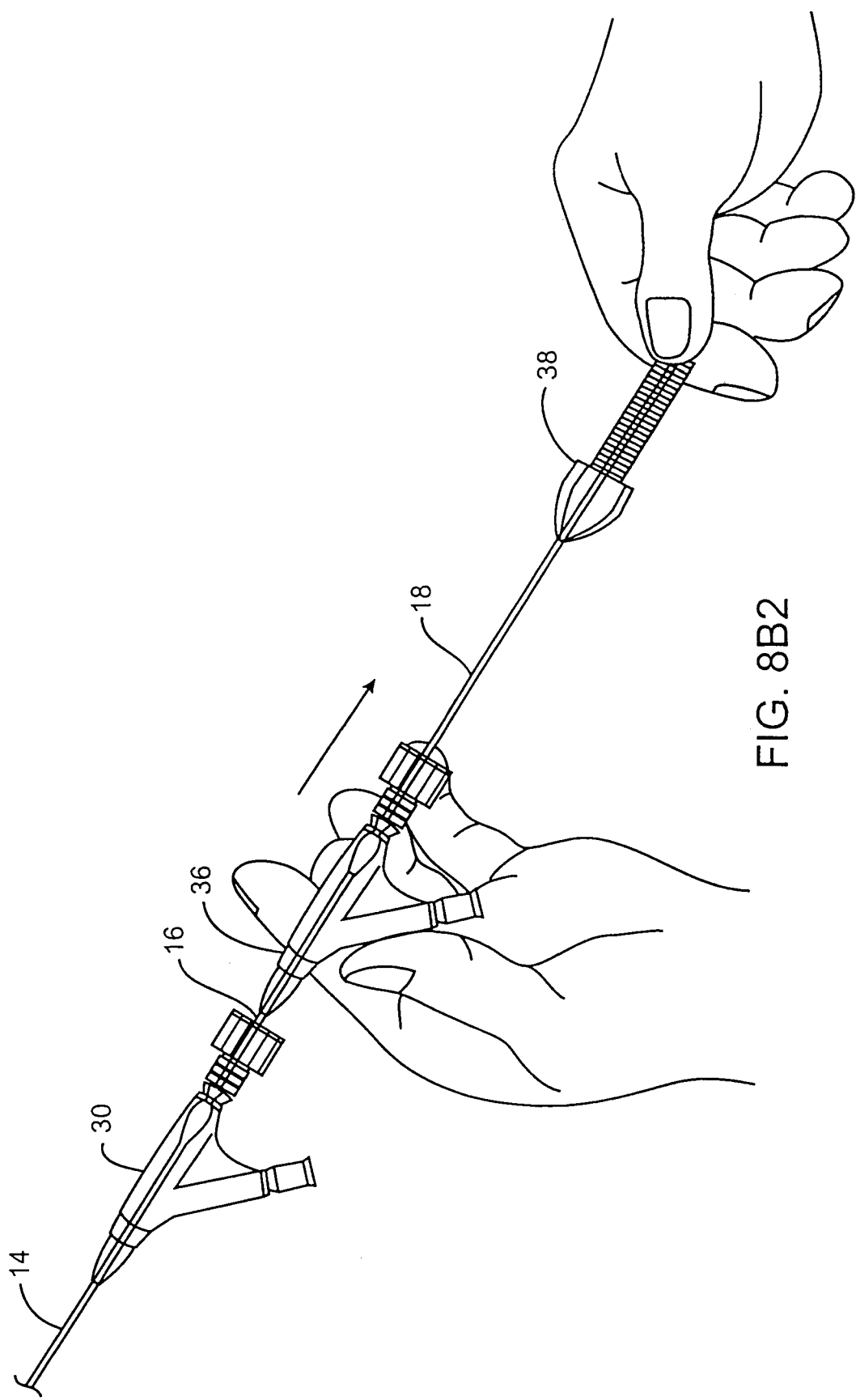
FIG. 8B2

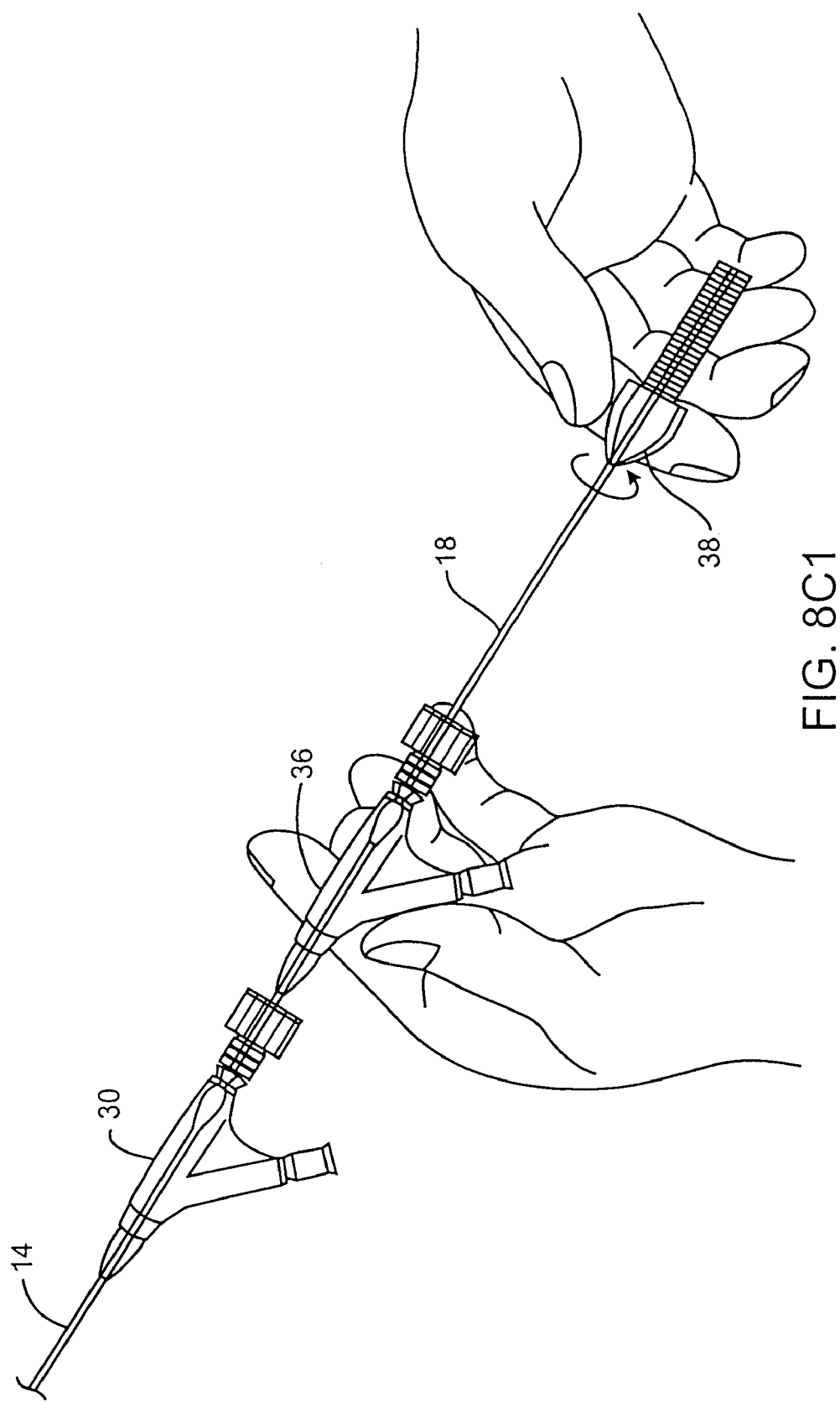

INSERTION/DEPLOYMENT CATHETER SYSTEM FOR INTRAFALLOPIAN CONTRACEPTION

CROSS-REFERENCE TO RELATED APPLICATION

The present patent application is a continuation of application Ser. No. 09/644,277 filed Aug. 22, 2000, now U.S. Pat. No. 6,763,833 which claims the benefit of priority from Provisional Application No. 60/150,521 filed Aug. 23, 1999, the full disclosure of which is incorporated herein by reference. The subject matter of this application is related to that of application Ser. No. 09/644,287 filed Aug. 22, 2000, which is entitled "Deployment Actuation System for Intrafallopian Conception", which has issued as U.S. Pat. No. 6,709,667, the full disclosure of which is incorporated herein by reference.

BACKGROUND OF THE INVENTION

The present invention generally relates to contraception and/or sterilization, and more particularly to temporary or permanent intrafallopian contraceptive devices, delivery systems, and non-surgical methods for their deployment.

While the theoretical effectiveness of existing non-surgical contraceptive techniques, including barrier methods and hormonal therapies, is well established, the actual effectiveness of most known methods is disappointing. One reason for these disappointing results is that many of the presently available methods for inhibiting pregnancy without surgery depend upon significant user involvement. Non-compliance typically results in quite high rates of failure, and overcoming user non-compliance to improve overall efficacy has proven quite difficult.

One form of long term contraception which is less susceptible to user non-compliance is the intrauterine device (IUD). IUDs have been found to have higher rates of reliability, and are effective for a longer period of time, then most other commercially available contraceptives. Unfortunately, IUDs are also associated with serious infectious complications. For this reason, the use of IUDs within the United States has decreased dramatically. Additionally, IUDs are subject to unplanned expulsion, and are removed due to excessive pain or bleeding in a significant percentage of cases, further reducing acceptance of the IUD as a method of inhibiting pregnancy.

Commercially available options for permanent sterilization include fallopian tube ligation and vasectomy. These methods are surgical and are not available to many people in the world. It is common knowledge that fertilization occurs in the fallopian tubes where the sperm and ovum meet. Tubal ligation avoids this by surgical and complete occlusion of the fallopian tubes.

In work done in connection with the present invention, it has previously been proposed to transcervically introduce a resilient coil into a fallopian tube so as to inhibit conception. PCT Patent Application No. 99/15116, assigned to the present assignee (the full disclosure of which is incorporated herein by reference) describes devices which are transcervically inserted into a tubal ostium and mechanically anchored within the fallopian tube. The described devices may promote a tissue ingrowth network to provide long term conception and/or permanent sterilization without the need for surgical procedures, and should avoid the risks of increased bleeding, pain, and infection associated with intrauterine devices.

While the recently proposed intrafallopian contraceptive devices represent a significant advancement in the art, still further improvements would be desirable. In general, it would be desirable to provide improved non-surgical devices, systems, and methods for inhibiting pregnancy. It would be beneficial if these improved techniques increased the ease with which these contraceptive devices could be deployed, and if the improvements further enhanced the long term retention of the contraceptive device once it has been deployed. It would be further beneficial if these improved access and deployment techniques were suitable for a wide variety of physiological geometries, ideally without having to tailor the device, deployment system, or deployment method for specific individuals. Some or all of these advantages are provided by the devices and methods described hereinbelow.

SUMMARY OF THE INVENTION

The present invention generally provides improved contraceptive and/or sterilization methods, systems, and devices. The invention generally improves the ease, speed, and reliability with which a contraceptive device can be deployed transcervically into an ostium of a fallopian tube. In many embodiments, a distal portion of the contraceptive device will function as a guidewire, facilitating advancement of the device (and the deployment system) into the tubal ostium. Typically, a proximal portion of the device will remain covered by a deployment sheath until the device is in position. Thereafter, the sheath can be withdrawn proximally, exposing a surface which is well adapted for retaining the device within the tube and/or uterotubal junction (but which would not be ideal for facilitating advancement of the device if left unsheathed during positioning). In the exemplary embodiment, the proximal portion remains in a small profile configuration while the sheath is withdrawn proximally, and is thereafter expanded to a large profile configuration engaging the surrounding tissues. Actuation may be affected after withdrawal of the sheath by a variety of mechanisms, ideally by restraining a helical coil of the proximal portion using first and second elongate bodies. Releasing one of the bodies relative to the other can release the exposed helical coil to expand resiliently. The released helical coil can safely engage and anchor the contraceptive device within a wide variety of physiological tissue geometries. Using the distal end of the contraceptive device as a guidewire avoids the complexity of multiple step deployments (which might otherwise involve separate guidewire access, catheter access, and advancement of the device), while still providing a smooth, easily advanced outer system profile.

In a first aspect, the invention provides a contraceptive method comprising guiding a contraceptive device distally into an ostium of a fallopian tube with an exposed distal portion of the contraceptive device while a sheath covers a proximal portion of the contraceptive device. The proximal portion of the guided contraceptive device is uncovered by withdrawing a sheath proximally from the proximal portion. The uncovered contraceptive device is released so that the contraceptive device inhibits conception.

Typically, the contraceptive device comprises an axially elongate flexible structure. Advantageously, the proximal portion of this flexible structure can be supported by the surrounding sheath while the distal portion is acting as a guidewire. Often times, at least a portion of the exposed distal portion can be supported with a core support (for example, a removable core wire) disposed within an axially oriented lumen of the contraceptive device. Preferably, the distal portion will flex laterally to track through the uterotubal junction so that the contraceptive device is positioned across the muscular lumen narrowing adjacent of the uterotubal junction. A distal ball tip having a diameter in a range from about 0.020 inches to 0.050 inches can help avoid perforation and facilitate tubal navigation.

In another aspect, the invention provides a contraceptive method comprising inserting a contraceptive device distally into an ostium of a fallopian tube. A proximal portion of the inserted contraceptive device is uncovered by withdrawing a sheath from around the proximal portion. An expandable structure of the proximal portion is maintained in a small profile configuration during the uncovering step so as to avoid restricting movement of the sheath while the sheath is withdrawn. The uncovered expandable structure is radially expanded to a large profile configuration so as to affix the contraceptive device within the ostium. The uncovered contraceptive device is released so that the contraceptive device inhibits conception.

Preferably, the expandable portion is maintained in the small profile configuration using a restraining force or torque. This restraint can be transmitted proximally using a first elongate body and a second elongate body. Typically, the first and second elongate bodies sustain a wind-down torque on the expandable structure. The expandable structure can be expanded by actuating the proximal handle so as to rotationally and/or axially release a proximal end of the elongate bodies relative to each other.

In another aspect, the invention provides a contraceptive system comprising an intrafallopian contraceptive device having a proximal portion adjacent a proximal end and a distal portion adjacent a distal end. The distal portion has a flexibility suitable to function as a guidewire. A sheath is releasably secured over the proximal portion of the contraceptive device so that the distal portion of the contraceptive device remains exposed when the contraceptive device and sheath are inserted transcervically into an ostium of the fallopian tube. A first elongate body extends from a proximal end distally into detachable engagement with the contraceptive device for withdrawing the sheath from around the inserted contraceptive device.

In yet another aspect, the invention provides a contraceptive kit comprising a contraceptive device and instructions for deploying the contraceptive device. The instructions describe the method steps of guiding the contraceptive device into an ostium of a fallopian tube with a distal portion of the contraceptive device. The instructions also describe uncovering a proximal portion of the contraceptive device so that the proximal portion can restrain the contraceptive device within the ostium.

BRIEF DESCRIPTION OF THE DRAWINGS

FIG. 2 is a side view of a removable core wire of the contraceptive system of FIG. 1B.

FIG. 3 is a contraceptive device of the contraceptive system of FIG. 1B, in which an outer helical coil is in a large profile configuration.

FIG. 3A is an end view of the contraceptive device of FIG. 3.

FIG. 4 is a side cross-section of a distal end of a delivery catheter of the contraceptive system of FIG. 1B.

FIG. 4A is an axial cross-sectional view of the delivery catheter of FIG. 4.

FIGS. 8, 8A, 8A1, 8A2, 8B, 8B1, 8B2, 8C, 8C1, and 8D are illustrations schematically showing a method for deploying a contraceptive device using the system of FIG. 1A.

DESCRIPTION OF THE SPECIFIC EMBODIMENTS

The present invention provides a contraceptive device, system, and method which can be used to inhibit pregnancy, typically for the long-term inhibition of pregnancy, and often providing permanent contraception or sterilization. By introducing at least a portion of these contraceptive devices into an ostium of a fallopian tube, the risks of unplanned expulsion, pelvic pain, and infectious complications may be significantly reduced. Although the present invention may be included within a group of contraceptive techniques generally referred to as fallopian tube occlusion methods, the invention need not be advanced fully into the fallopian tube, and in some embodiments, need not fully block the tubal lumen to effectively disrupt fertilization. As described in U.S. patent application Ser. No. 09/324,078, assigned to the present assignee (the full disclosure of which is incorporated herein by reference), contraception may optionally be provided by fully occluding the tubal lumen, and/or by sufficiently disrupting the fertilization process without total occlusion. In some embodiments, including a bioactive material such as copper may enhance the device's effectiveness.

As used herein, a structure is inserted "within a tubal ostium" whenever the structure is advanced from the uterus into (and optionally beyond) the tubal ostium, the uterotubal junction, and/or the fallopian tubes.

Figure 1:
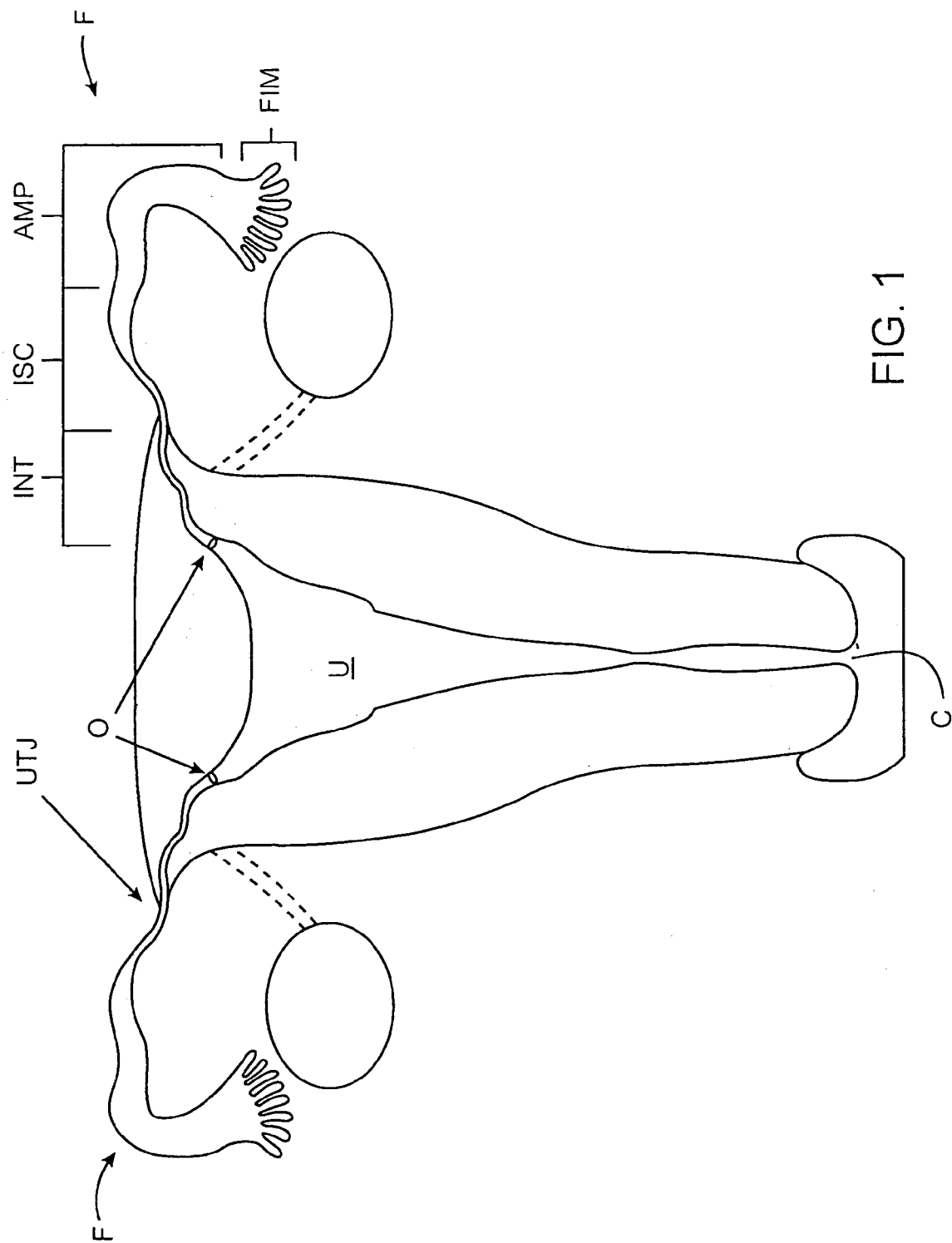
FIG. 1 illustrates the uterine and tubal anatomy for deployment of the contraceptive devices of the present invention.

Referring now to FIG. 1, access to uterus U will generally be gained through cervix C. From within uterus U, fallopian tubes F are accessed via tubal ostia O.

Fallopian tubes F generally include three segments between ostium O and the fimbria FIM. Beginning adjacent uterus U, the intramural segment INT of fallopian tubes F are surrounded by the muscular uterine tissues. Beginning at uterotubal junction UTJ, fallopian tubes F extend beyond the uterine tissues and within the peritoneal cavity along an isthmic segment ISC, and then along an ampullary segment AMP.

In general, the ideal placement for the intrafallopian contraceptive devices of the present invention is spanning the intramural INT to isthmic ISC portion of the fallopian tube. Where a radially expandable attachment mechanism such as an outer coil is included on the intrafallopian contraceptive device, that expandable or anchoring structure will preferably span the uterotubal junction UTJ. It should be noted that the uterotubal junction UTJ may be defined as the plane where the fallopian tube meets the peritoneal cavity. It should also be noted that the narrowest portion of the fallopian tube need not necessarily be disposed in the isthmic segment ISC, particularly once the contraceptive fallopian device (often having a radially expandable anchoring structure) is deployed therein. In fact, work in connection with the present invention has shown that the effectively narrowest portion of the tube may be at or adjacent the uterotubal junction UTJ.

Figure 1A:
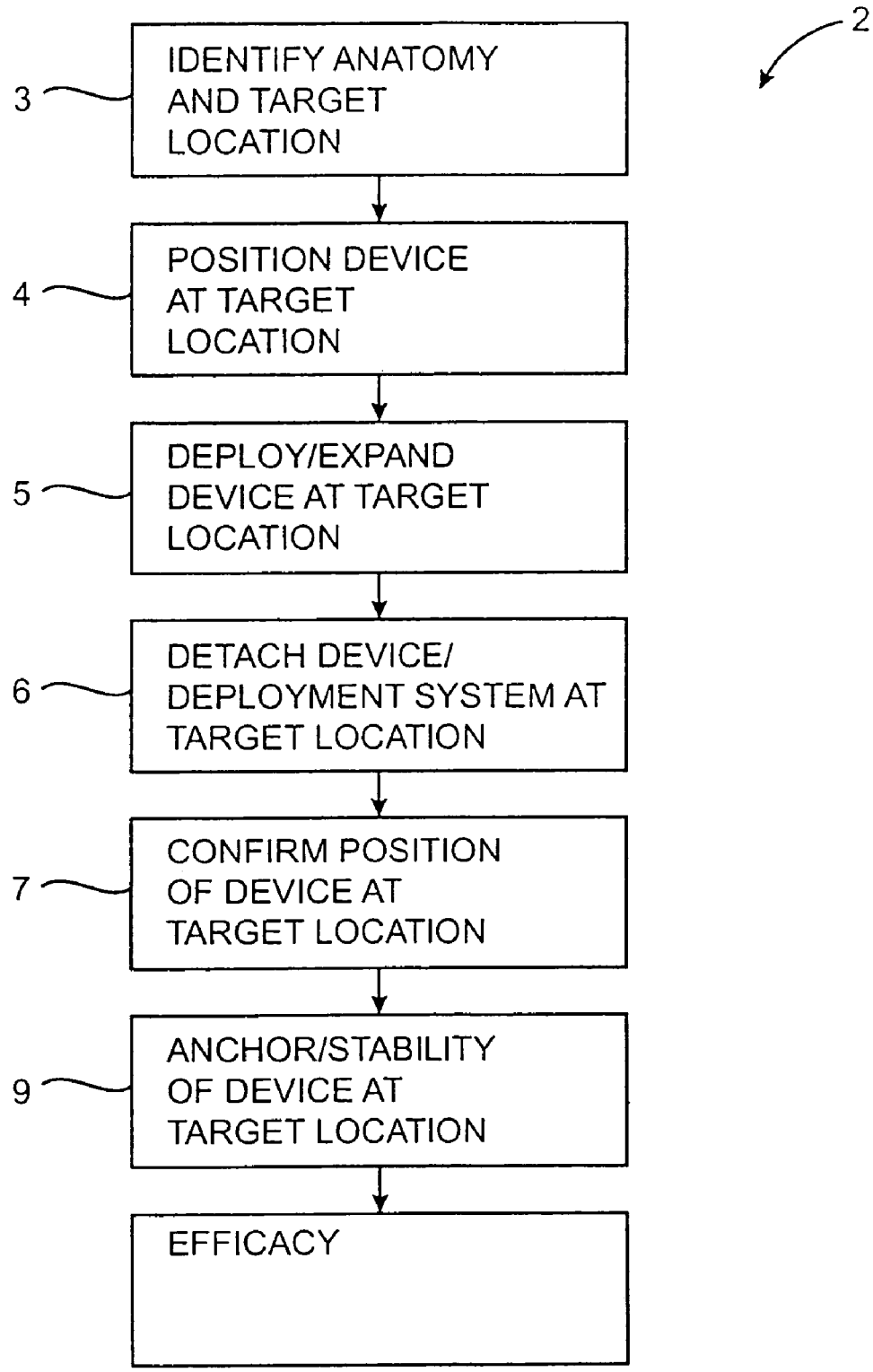
FIG. 1A schematically illustrates method steps for an exemplary contraceptive device deployment method.

Referring now to FIG. 1A, an overview of an exemplary method 2 for deploying and using the contraceptive devices of the present invention is helpful to understand the selection of structures used in those devices. It should be understood that not all steps need be performed in every deployment. Nonetheless, reviewing the exemplary deployment method 2 will help to understand the structures described hereinbelow.

Identification of the anatomy and target location 3 allows the operator to determine the preferred placement of the contraceptive device within the ostium, and also to determine if any special circumstances are present for a particular device placement procedure. Anatomy and target location identification can be facilitated using a variety of known visualization modes, including hysteroscopy, sonography (ultrasound), fluoroscopy, and the like. Hence, an exemplary contraceptive device may be adapted to delivery using more than one imaging modality.

The exemplary contraceptive device will also preferably be able to accommodate a wide variety of anatomies. Two factors contribute to the importance of this variability: First, a wide variation may be observed between tubal anatomies of differing patients. Secondly, it can be quite difficult to determine and identify the specific tubal anatomy of a particular patient. As a result, the preferred contraceptive device may incorporate safeguards allowing sufficiently accurate placement (with tolerance for normal operator error), as well as for the variance in the length and diameter of the various segments of the fallopian tube.

Exemplary deployment method 2 in FIG. 1A will also include positioning of the device at the target location 4. Once again, a wide variety of techniques might be used to assist a healthcare professional in positioning the device in the correct location, including visualization techniques, providing high-contrast markers (such as radiopaque markers, echogenic markers, or the like), providing tactile indication of the placement position by including physical stops or "bumpers" (which may be adapted to engage reference tissues in such a tactile way as to send a signal to the healthcare professional), or the like. Device positioning can be significantly facilitated by providing an appropriate device and/or deployment system design having the proper flexibility, navigation characteristics, friction reduction surfaces, small delivery profile, coatings, and the like. Once again, device positioning 4 will preferably compensate for anatomical variations, operator error, and difficulties in visualization so as to help promote accurate placement.

In the exemplary deployment method 2, the device is deployed and/or expanded at the target location in the step indicated by reference numeral 5. Optionally, the device and/or deployment system may allow visualization and/or confirmation of device expansion while expansion takes place.

Generally, the contraceptive device will be detached from its deployment system at the target location in step 6. Once again, it is helpful to provide visualization and/or confirmation of detachment, which may be provided visually, via ultrasound, fluoroscopy, or the like. It should be understood that a wide variety of detachment mechanisms might be used to decouple the device from the deployment system.

In the exemplary method, it should be possible to confirm the position of the device at the target location 7. Confirmation may be provided, once again, by visualizing at least a portion of the device after detachment, often using the same visualization modality used during placement. In addition to optical visualization techniques, this may be provided by including radiopaque markers for fluoroscopic placement confirmation, sonographic markers for ultrasound placement confirmation, or the like. Optionally, specific marker locations may be provided along the contraceptive device 2, for example, to indicate the specific locations of proximal and/or distal ends of the device.

Exemplary method 2 further includes a step 9 for anchoring and stability of the device at the target location. Aspects of this step include accommodating visualization of the device so as to monitor it's stability. Anchoring of the device at the target location may include anchoring on an acute basis (such as using an expanded helical coil that can adjust and adapt to variations in the tubal lumen, an expanded stent-like structure, expanded braid, or the like) and long-term (such as may be provided by including a fiber mesh or lattice which incites a tissue reaction such as ingrowth, thereby providing fibrous tissues which affix the device in place within the fallopian tube). Similarly, stability will preferably be provided for both a short-term and a long-term, typically by designing a device with the proper resiliency and shape to accommodate physiological movement without shifting. The device will preferably be wear-profile balanced to provide sufficient anchoring without inducing pain or losing its stability due to erosion for the life of the patient.

The final step indicated on the exemplary method 2 of FIG. 1A is efficacy. This may be provided by incorporating a lumen/space filling design that sufficiently alters the function and architecture of the fallopian tube so as to inhibit conception. This may include the use of polyester fibers or the like to incite the desired tissue reaction.

In general, the devices of the present invention may be adapted to incite a reaction tissue response in the fallopian tube through the presence polyester fibers, or the like. Ideally, this reaction can be classified as a highly localized, benign tissue reaction. The reaction results in the incorporation of the contraceptive device into the tubal lumen tissues, so that the device is firmly embedded into the surrounding tissue structure. This reaction can typically be characterized by the proliferation of smooth muscle cells and associated fibrosis. Additionally, the tubal lumen will generally exhibit an absence of the normal tubal architecture which is generally necessary for conception. The tubal lumen may also be obstructed, occluded, and/or functionally occluded by the presence of the device and associated fibrosis sufficiently to inhibit conception. The reaction is a benign one, and there appears to be no change in anatomy or structure of the outer tubal wall beyond approximately 5 to 10 mm radially outwardly from the outer coil of the device. Similarly, normal tubal architecture will often be visible about 5 mm axially beyond the device (typically distal of the device, as the device often extends into the uterus), again indicating a very localized reaction.

Figure 1B:
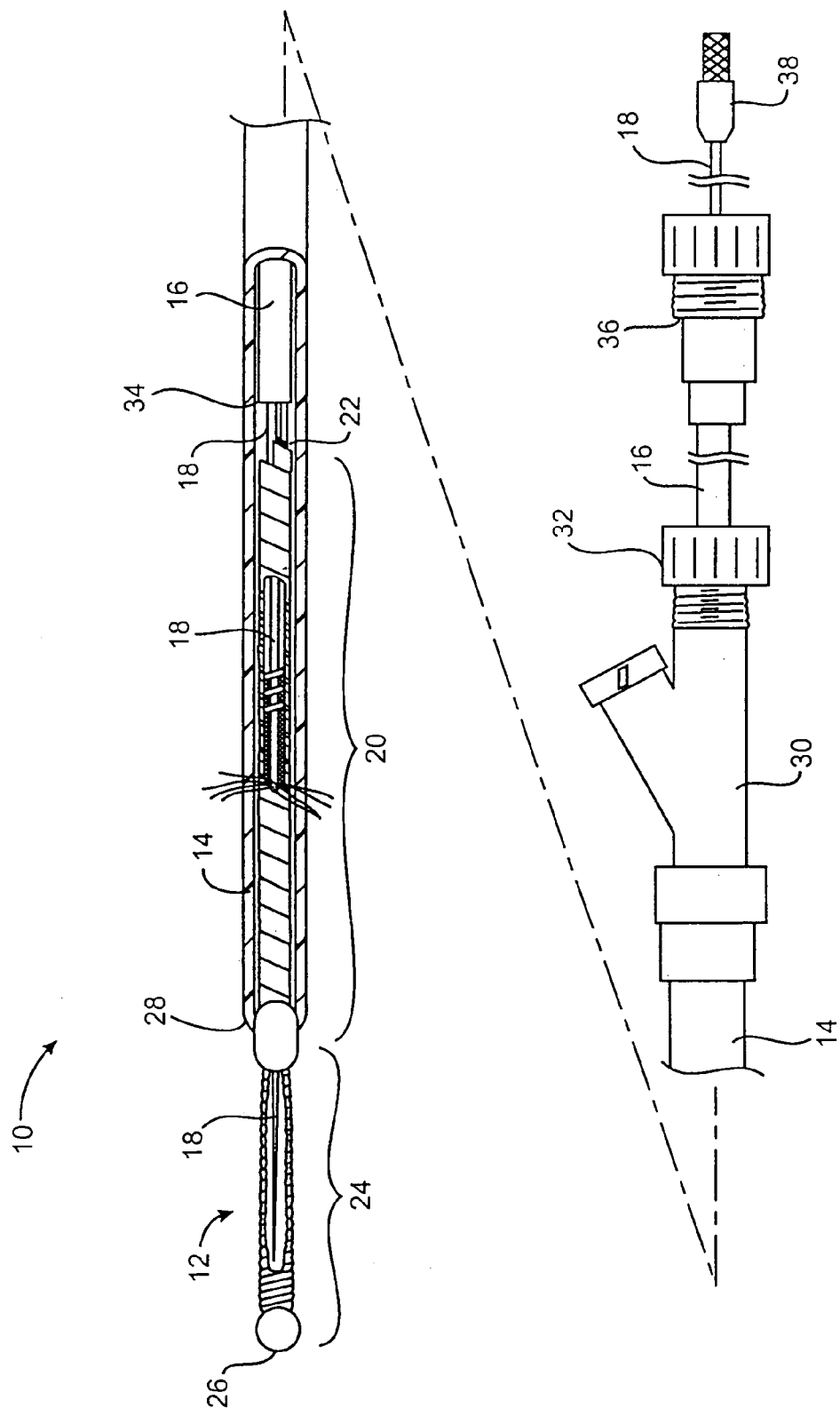
FIG. 1B is a partial cut-away side view of a contraceptive system according to the principles of the present invention.

Referring now to FIG. 1B, an exemplary contraceptive system 10 generally includes a contraceptive device 12, a sheath 14 partially surrounding the contraceptive device, a release catheter 16, and a core shaft 18. Contraceptive device 12 generally has a proximal portion 20 adjacent a proximal end 22 (disposed within sheath 14), and a distal portion 24 adjacent a distal end 26 (which are exposed beyond the distal end of sheath 14). Distal portion 24 generally functions as a distal guidewire while system 10 is advanced within the tubal ostium. Proximal portion 20 includes a radially expandable structure which can be expanded after sheath 14 is withdrawn so as to affix the contraceptive device in the deployed position.

Sheath 14 is generally a tubular structure having a distal end 28 and extending proximally to a proximal housing 30. Sheath 14 will generally have a length in a range from about 25 to about 50 cm, and will typically have an outer diameter in a range from about 0.020 to about 0.060 inches, the exemplary sheath having a length of about 39.5 cm and an outer diameter of about 0.04 inches. The inner diameter of sheath 14 may be in a range from about 0.02 inches to about 0.05 inches, with the exemplary sheath having an inner diameter of about 0.033 inches. Proximal housing 30 includes a side arm with an injection port to allow infusion of fluids for patency checks, delivery of local anesthetic, or the like. Proximal housing 30 also includes a Touhy-Borst valve 32 releasably securing sheath 14 to release catheter 16.

Release catheter 16 generally comprises a tube having a distal end 34 which releasably engages contraceptive device 12, and a proximal end adjacent a proximal fitting 36. Release catheter 16 will generally be longer than sheath 14, and fitting 36 will include another Touhy-Borst valve releasably securing release catheter 16 to core shaft 18. The release catheter length is sufficiently longer than the sheath 14 so that full retraction of the sheath exposes the distal end of the release catheter, thereby allowing the release of the expandable structure upon movement of the release catheter to be hysteroscopically monitored. It should be understood that the Touhy-Borst valve may be replaced by any coupling structure which inhibits axial and rotational movement between the coupled devices, such as a key-slot arrangement or the like.

In the exemplary embodiment, core shaft 18 comprises a resilient tapering structure extending from within distal portion 24 of contraceptive device 12 proximally through fitting 36 of release catheter 16 to a proximal handle 38. Core shaft 18 threadably engages contraceptive device 12 proximally of distal end 28 of sheath 14 before deployment. In the exemplary embodiment, core shaft 18 and release catheter 16 transmit a wind-down torque onto an expandable structure of the contraceptive device so as to maintain the expandable structure in the small profile configuration. Hence, release catheter 16 relative to releasing core shaft 18 by actuating the Touhy-Borst valve of fitting 36 allows the expandable structure to be activated independently of movement of the surrounding sheath.

While exemplary contraceptive device 12 makes use of a radially expandable helical coil to help restrain the structure during tissue ingrowth, a wide variety of mechanical and other restraint mechanisms might be included. For example, alternative mechanical anchors might be attached to the device, such as resilient coils biased to form bends, loops, and/or other secondary shapes having enhanced cross-sections, slotted tubes, Malecot-type structures, radially expandable braids, stent-like devices, and the like. The mechanical structures may be resilient, plastically deformable, or the like, and suitable structures are described in more detail in, for example, PCT Publication No. WO 99/15116.

Still further device-restraint techniques might be employed, including thermal, chemical, adhesive, and the like. These techniques can be used to avoid expulsion by increasing friction between the device and the surrounding tissues, by imposing limited tissue damage to promote scar tissue formation, and/or by promoting tissue ingrowth into the device. Thermal techniques may include, for example, transmission of electrical or laser energy along contraceptive system 10. Resistive heating of contraceptive device 10 might be effected by applying an electrical potential across the device with conductors extending along sheath 14 and release catheter 16, laser energy along an optical wave guide attached to core wire 18, or the like. Monopolar tissue desiccation might be effected via a large return electrode patch by energizing core wire 18 with radiofrequency energy, or an adhesive and/or caustic agent (such as a cyanoacrylate or silver nitrate) might be introduced via any of the lumens of the delivery system, via a dedicated lumen or structure, or the like. Biodegradable plugs and the like might also be included, and the retained structure may optionally comprise copper or other bioactive agents to help inhibit conception.

Tissue reaction to the retained contraceptive device 12 can help to provide long term contraception and/or sterilization. To promote conception inhibiting tissue reaction, device 12 will often include a tissue reaction material, the material often comprising fibers. The fibers may comprise a polyester, such as Dacron® polyesters, silk, nylon, or the like. The fibers may be in the form of a weave, a knit, a braid, a felt, or the like, or may comprise stands attached to the device body.

The components of contraceptive system 10 can be further understood with reference to FIGS. 2 through 5, in which these components are illustrated individually. Beginning with FIG. 2, core shaft 18 tapers to a gradually increasing diameter proximally of distal end 40 so as to provide increasing support of distal portion 24, proximal portion 20, and the catheter structures proximal of contraceptive device 12. This increasing support (and the associated increase in column strength) enhances the pushability of the contraceptive system while accessing the target deployment site. Threads 42 threadingly engage a coil of the contraceptive device, and are generally formed by affixing a coil with separated windings to a central core wire at a bond 44. A tube 43 may also be affixed at bond 44 to prevent binding and/or jumping of the cooperating threads, the tube ideally comprising stainless steel, platinum, or the like.

In the exemplary device, core wire 18 comprises a high strength metallic structure having a diameter in a range from about 0.003 inches to about 0.037 inches. The ideal core wire has a total length of about 65 cm between distal end 40 and proximal handle 38, while threads 42 are separated from the distal end by a distance of about 3 cm. Core wire 18 tapers from a minimum diameter of about 0.003 inches near the distal end to a diameter of about 0.011 inches adjacent threads 42, and to a maximum diameter of about 0.029 inches proximally of the threads. The exemplary core wire comprises nickel titanium, while threads 42 comprise stainless steel attached to the central wire by a bond 44 of silver tin.

While the exemplary system uses threads to couple the core wire (or other deployment shaft) with the contraceptive device, a variety of alternative detachable connections might be used, including cooperating keys/slots, BNC connectors, or the like. The exemplary contraceptive device 12 is illustrated in more detail in FIG. 3. Contraceptive device 12 includes a primary coil 50 which extends from a distal ball tip 52 to proximal threads 54, which may conveniently be formed by separating the proximal windings of the primary coil. The expandable structure, here in the form of a helical outer coil 56, has a proximal end bent to form a wind-down attachment 58, and has a distal end affixed to coil 50 at coil bond 60. Fiber 62 extends between the inner and outer coils, and is also disposed within primary coil 50 so as to promote tissue ingrowth throughout the cross-section of contraceptive device 12. The arrangement of coil attachment 58 and position of fiber 62 can be seen in the axial view of FIG. 3A. By making use of a contraceptive device having a distal portion 24 which can act as a guidewire, no open lumen need be provided through the center of the contraceptive device (for example, for a separate guidewire), and multiple access/deployment steps (for example, accessing the target location with a guidewire, advancing a catheter over the guidewire, removing the guidewire from the positioned catheter, and then advancing the contraceptive device) can be avoided.

Figure 3B:
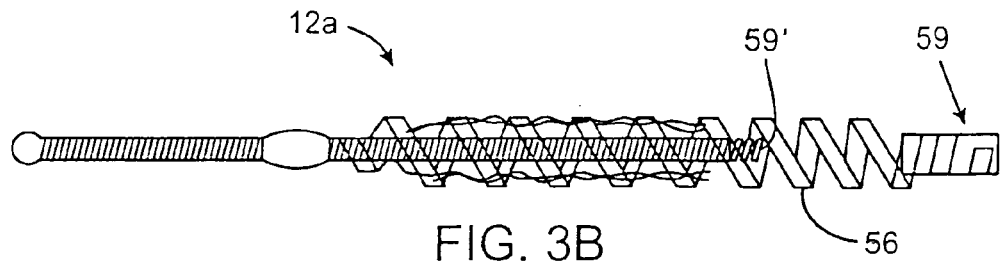
FIG. 3B illustrates a contraceptive device having a tubular band for smoothly disengaging a release pin of a release catheter.

A slight variation upon the wind-down attachment is illustrated in FIG. 3B. An alternative contraceptive device 12a includes a small tube or band 59 soldered within a small diameter proximal section of outer coil 56. Band 59 can have a relatively large interface area with coil 56 to facilitate bonding, avoids stress concentrations, and presents a smooth inner lumen which may inhibit binding of the release catheter. Band 59 may comprise stainless steel or platinum, ideally having an inner diameter of about 0.023 inches and an outer diameter, with the thickness of the surrounding outer coil and solder bond, of about 0.03 inches. A similar band 59' may be disposed within threads 54 of coil 50 to provide a radiopaque marker, and to inhibit thread jump. Band 59' may be similar in structure to band 59, but shorter in length. Still further alternative attachment mechanisms are possible. For example, a mass or knob may be formed at the proximal end of outer coil 56 from a simple ball of solder or coil material, bend, or the like, which is slidably receivable within a slot or other opening of the delivery catheter.

In the exemplary embodiment, coil 50 is formed of a high strength resilient material, ideally comprising stainless steel wire having a diameter of about 0.005 inches, and wound to form a coil having an outer diameter of about 0.022 inches. Ball tip 52 preferably has a cross-section which is larger than the cross-section of coil 50, the ball tip generally having a diameter in a range from about 0.020 inches to about 0.050 inches, the exemplary ball tip having a diameter of 0.027 inches.

Helical coil 56 comprises a highly elastic high strength metal which is biased to expand from the low profile configuration illustrated in FIG. 1 to the larger profile configuration illustrated in FIG. 3 when released within the target site. In the exemplary embodiment, outer coil 56 comprises a ribbon of a superelastic or shape memory alloy, and has a thickness in the range from about 0.001 inches to 0.002 inches and a width in a range from about 0.010 inches to 0.020 inches, with the ribbon being biased to form a helical coil having an outer diameter of about 0.080 inches and a length of about 3.5 cm when not otherwise restrained. Outer coil 56 is preferably fixed to primary coil 50 by a bond 60 of solder. Bond 60 will preferably be separated from ball tip 52 by a distance in a range from about 0.4 cm to about 0.7 cm. Advantageously, bond 60 may be aligned with the distal end 28 of sheath 14 so as to help present an atraumatic increase in diameter between distal portion 24 of contraceptive device 12 and the sheathed proximal portion 20 prior to deployment.

Fiber 62 may comprise a polyester or the like. The fiber may be loosely woven or matted strands, with at least one end of the fibers affixed to primary coil 50 or outer coil 56. In the exemplary embodiment, fiber 62 comprises between about 20 and 70 filaments of textured PET fibers.

Generally, the expandable structure will help hold contraceptive device 12 in place at least until tissue ingrowth occurs sufficiently so as to permanently retain the contraceptive device and/or may restrain the device permanently. Hence, the expandable structure will often benefit from a relatively high friction outer surface. Such an outer surface might make it difficult to advance the contraceptive device into position if the device is advanced without sheath 14.

Work in connection with the present invention has shown that resiliently expandable structures which have sufficient strength to reliably hold the contraceptive device within the ostium of the fallopian tube may impose significant frictional forces against a surrounding sheath. These frictional forces can significantly complicate the accurate delivery of contraceptive device. Hence, outer coil 56 is preferably maintained in a small profile configuration within sheath 14 by applying a wind-down torque between core wire 18 and release catheter 16. The core wire can transfer the wind-down torque to outer coil 56 through cooperating threads 42, 54, with the direction of the wind-down torque preferably being arranged so that the wind-down torque discourages decoupling of the threads. In other words, rotation of core wire 18 relative to contraceptive device 12 in a direction opposed to the wind-down torque is used to detach core wire 18 from contraceptive device 12. It should be understood that a variety of alternative deployment/expansion mechanisms might be used with alternative expandable structures, such as stent-like expandable structures, braids, etc.

The distal structure of release catheter 16 is shown in FIGS. 4 and 4A. The wind-down torque is releasably transferred between outer coil 56 and release catheter 16 by cooperation between bend 58 and pin 66 at the distal end 34 of the release catheter 16. Release catheter 16 generally includes a tubular body 68 formed of polyimide. Pin 66 is disposed within a lumen of tubular body 68, and is supported within the tubular body by a helical support coil 70 and adhesive 72. Pin 66 comprises a stainless steel bar having a width of about 0.008 inches, a thickness of about 0.003 inches, and a total length of about 1 cm, and extends distally from distal end 34 by a distance of about 3 mm. Support coil 70 also comprises stainless steel, and the support coil and pin 70 are bonded within tubular body 68 by cyanoacrylate, with the exemplary tubular body having an inner diameter of about 0.030 inches and an outer diameter of about 0.033 inches. Interestingly, these tubular body dimensions may be driven by the wind-down torque transferred proximally by release catheter 16. Optionally, the device and/or delivery system may be adapted to facilitate visualization and/or confirmation that release is successful. For example, the outer coil may look visibly different before and after deployment due to gaps in the coil winding, or the like. Similar feedback may be provided by fluoroscopic or sonographic image changes.

Figures 5A, 5C, 5E:
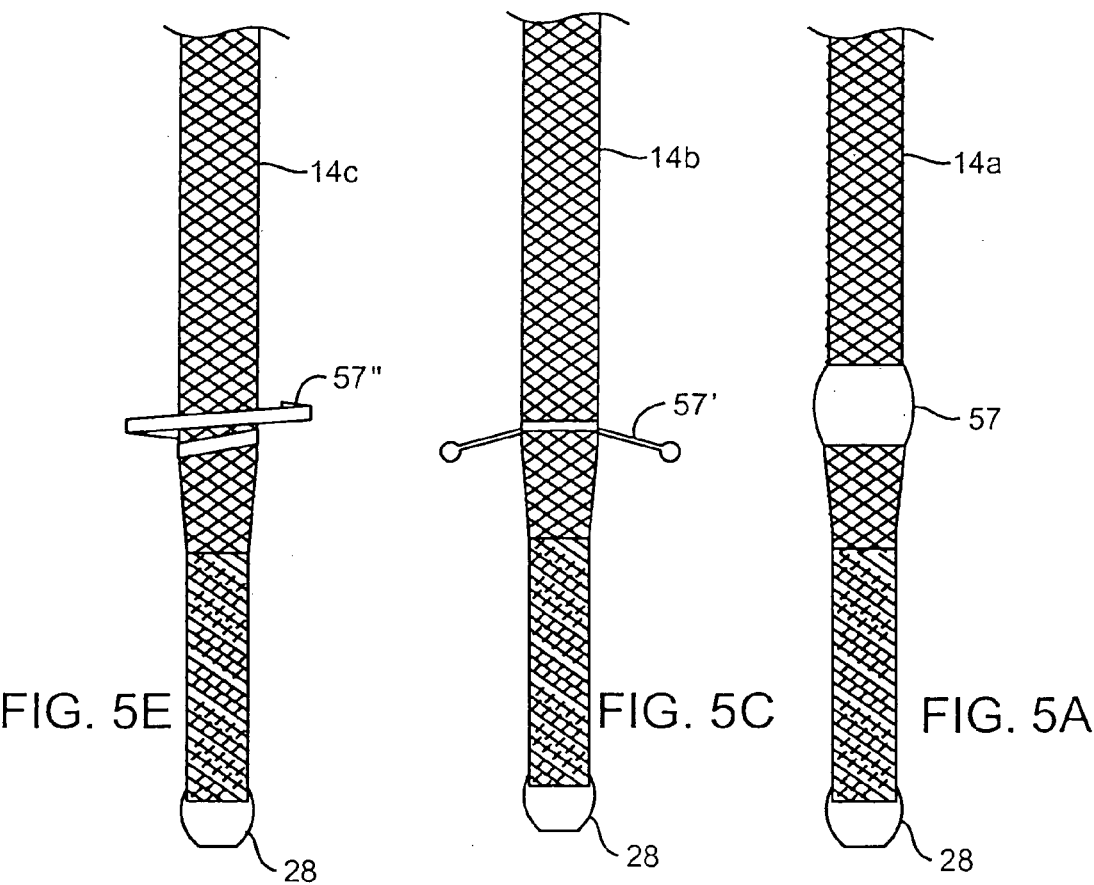
FIGS. 5A through 5F illustrate sheaths having positioning surfaces for axially positioning the contraceptive device relative to the tubal ostium.
Figures 5B, 5D, 5F:
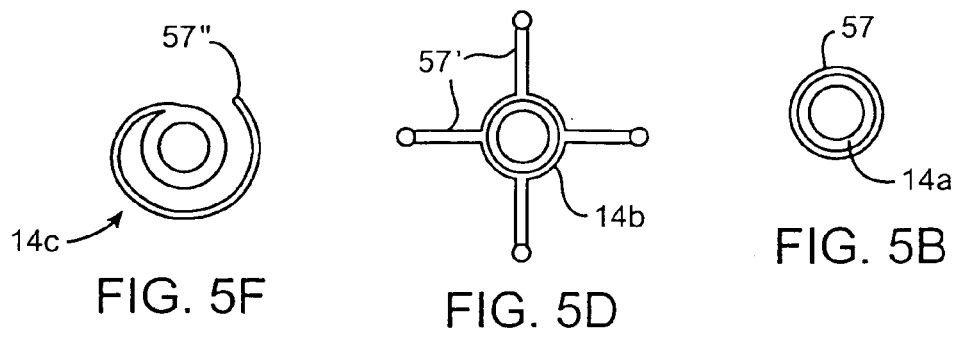
Figure 5:
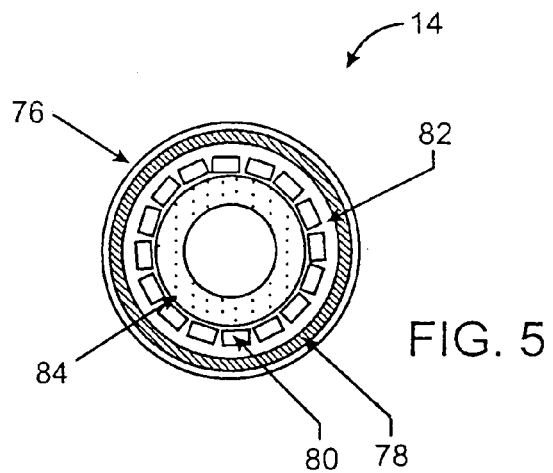
FIG. 5 is an axial cross-sectional view of an outer sheath of the delivery system of FIG. 1B.

The structure of sheath 14 is illustrated in more detail in FIG. 5. Distal end 28 (see FIG. 5A) of sheath 14 will preferably be rounded, with the distal end ideally cooperating with coil bond 60 of contraceptive device 12 so as to avoid friction and facilitate distal navigation of delivery system 16 through the uterotubal junction and into the fallopian tube. The rounded distal end 28 may optionally be rounded along both the inner and outer diameter of sheath 14, or may primarily be rounded along the outer diameter so as to taper inwardly distally.

Sheath 14 will preferably have a multi-layer structure, with the layers comprising (beginning at the outside) a hydrophilic coating 76 to reduce friction during tracking and navigation. Such hydrophilic coatings become quite slippery when exposed to fluid. Below hydrophilic coating 76 is a structural layer of a polymer 78 such as Tecoflex™ along the proximal portion of sheath 14, and a reinforcing braid 80 of a metal, ideally of stainless steel, is disposed within a layer of polyimide below polymer layer 78. Along the more distal portion of sheath 14, metal braid 82 is disposed within polymer layer 78 of Tecoflex™, or the like, and the polyimide layer is absent so as to provide enhanced flexibility. The inner lumen of sheath 14 is defined by a low friction polymer coating 84, the low friction polymer ideally comprising a PTFE such as Teflon®. Suitable sheaths 14 may be commercially available from a variety of vendors. Exemplary structures may be described in more detail in published PCT patent application WO 98/57589, the full disclosure of which is incorporated herein by reference.

As schematically illustrated in FIGS. 5A through F, alternative sheaths 14A, B, and C, include bumpers 57, 57', and 57", respectively. Bumper 57 has an outer surface extending radially from the outer surface of the underlying sheath. Although bumper 57 may optionally provide a tactile indication that the sheath 14A is advancing distally beyond the target deployment position, it does not necessarily prevent the sheath from advancing so that the bumper can enter into the tubal ostium. Bumper 57 may also provide a visible marker that hinders pushing of the sheath so that the bumper moves past the ostium. Optionally, bumper 57 may comprise a colored adhesive, or may comprise a clear adhesive with a colored band of material disposed underneath.

Alternative bumpers 57' and 57" may comprise polymer or metallic structures, ideally comprising a polyethylene or a super-elastic shape memory alloy. These radially expandable bumper structures can be collapsed for delivery through a working lumen of a hysteroscope, and can then expand to impede advancement of the sheath by engaging the uterine tissue adjacent to the tubal ostium.

Figure 6:
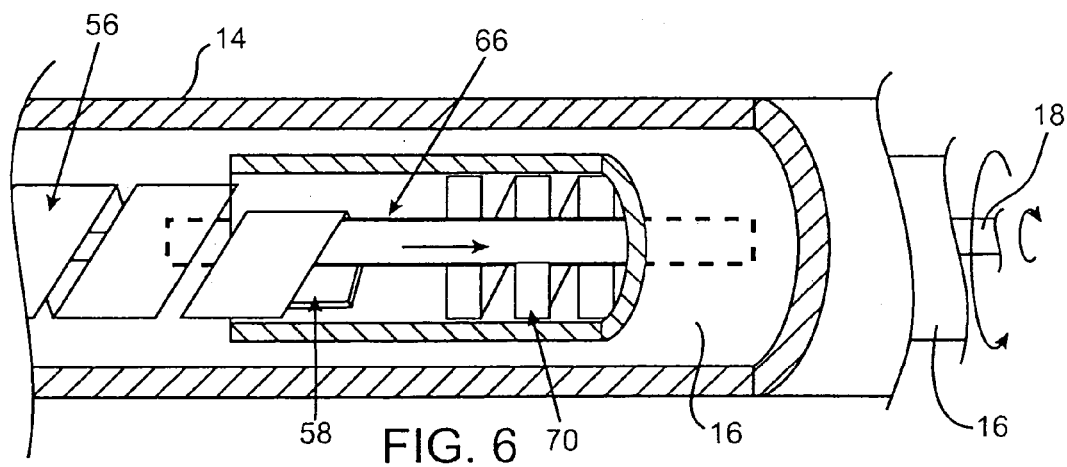
FIG. 6 is a partial cut-away view showing engagement between the outer helical coil of the contraceptive device and the release catheter so as to maintain the wind-down torque on the outer helical coil.

Referring now to FIG. 6, the sliding engagement between pin 66 of release catheter 16 and bend 58 of outer coil 56 is more clearly illustrated. FIG. 6 also shows how the wind-down torque imposed on the outer coil by the core shaft 18 and release catheter 16 help maintain the outer coil in a small profile configuration within sheath 14, allowing the sheath to be withdrawn easily. The wind-down torque can be released by sliding release catheter 16 so that pin 66 slides free of bend 58. Optionally, the release catheter may first be allowed to rotate relative to the core shaft to reduce the engagement forces between bend 58 and pin 66.

Figure 7:
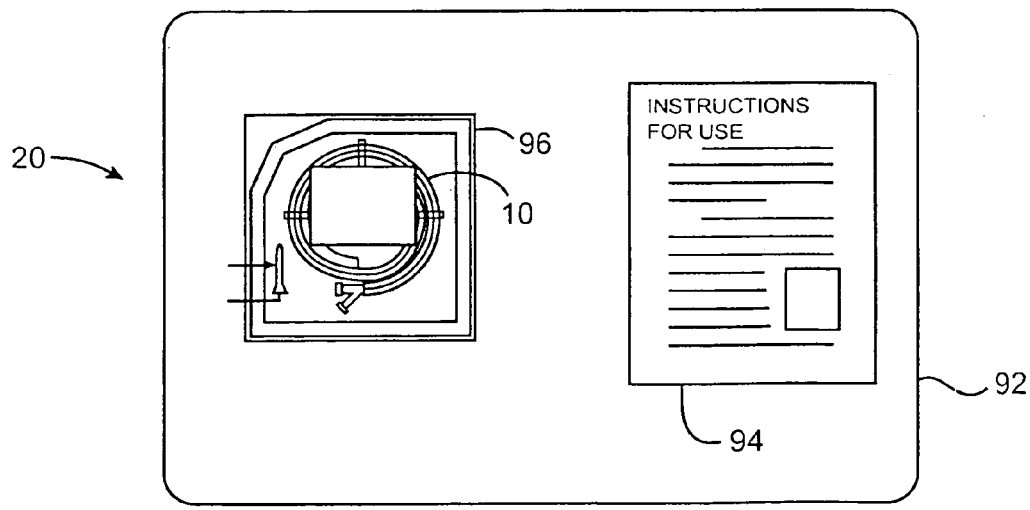
FIG. 7 schematically illustrates a contraceptive kit according to the principles of the present invention.

Referring now to FIG. 7, a contraceptive kit 90 generally includes packaging 92 containing delivery system 10 and instructions for its deployment 94. Contraceptive system 10 will generally be hermetically sealed within a sterile pouch 96. Alternatively, packaging 92 may hermetically seal the contraceptive system. Instructions for use 94 will describe method steps for deployment of the contraceptive system, as described herein. The instructions for use may comprise printed material, and/or may optionally include machine-readable code (such as a CD ROM, floppy disk, or the like) and/or graphical information (such as a video tape). In some embodiments, the instructions for use may at least in part be incorporated into packaging 92 or sterile pouch 96.

Figure 8:
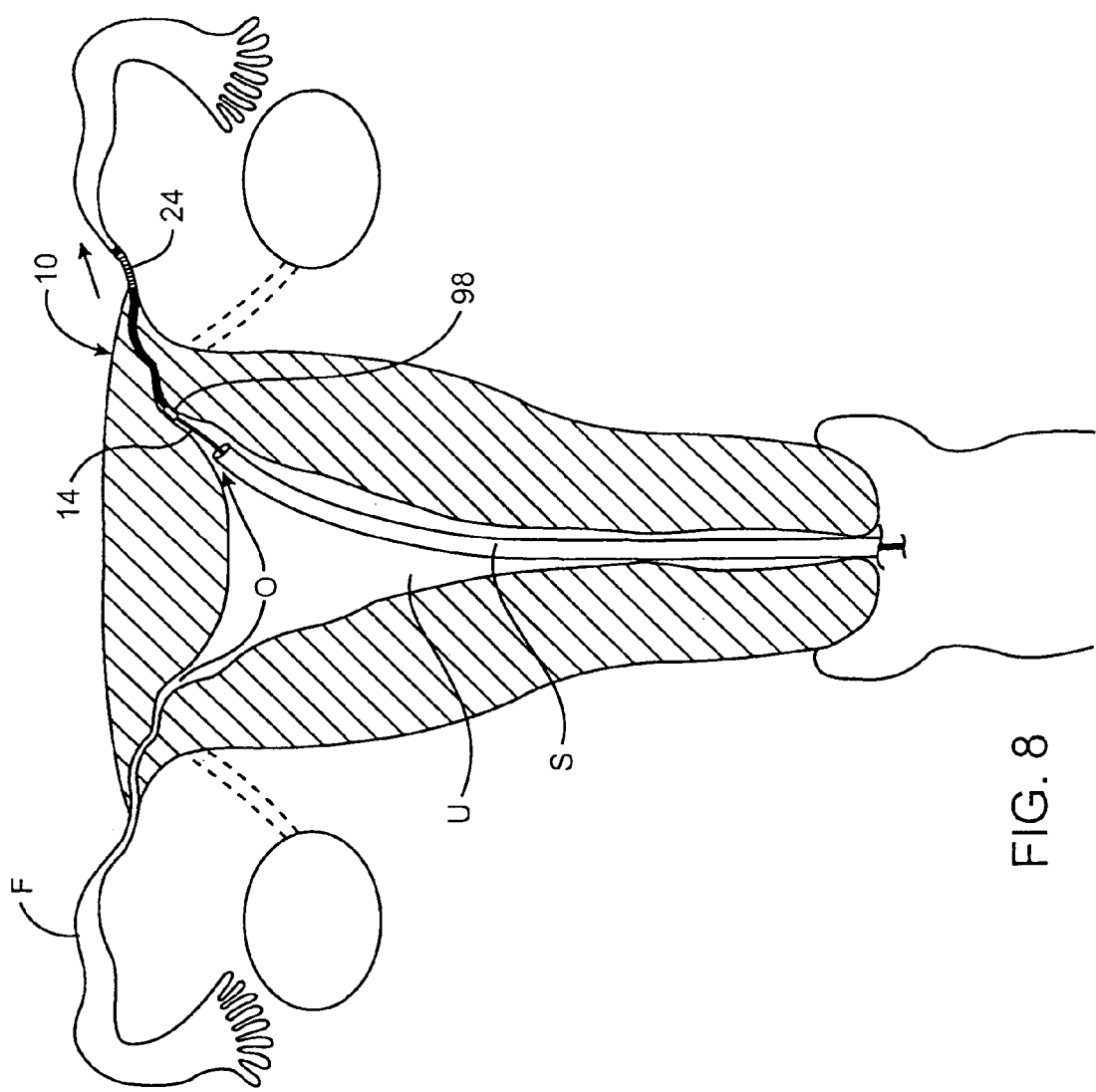
Figure 8A:
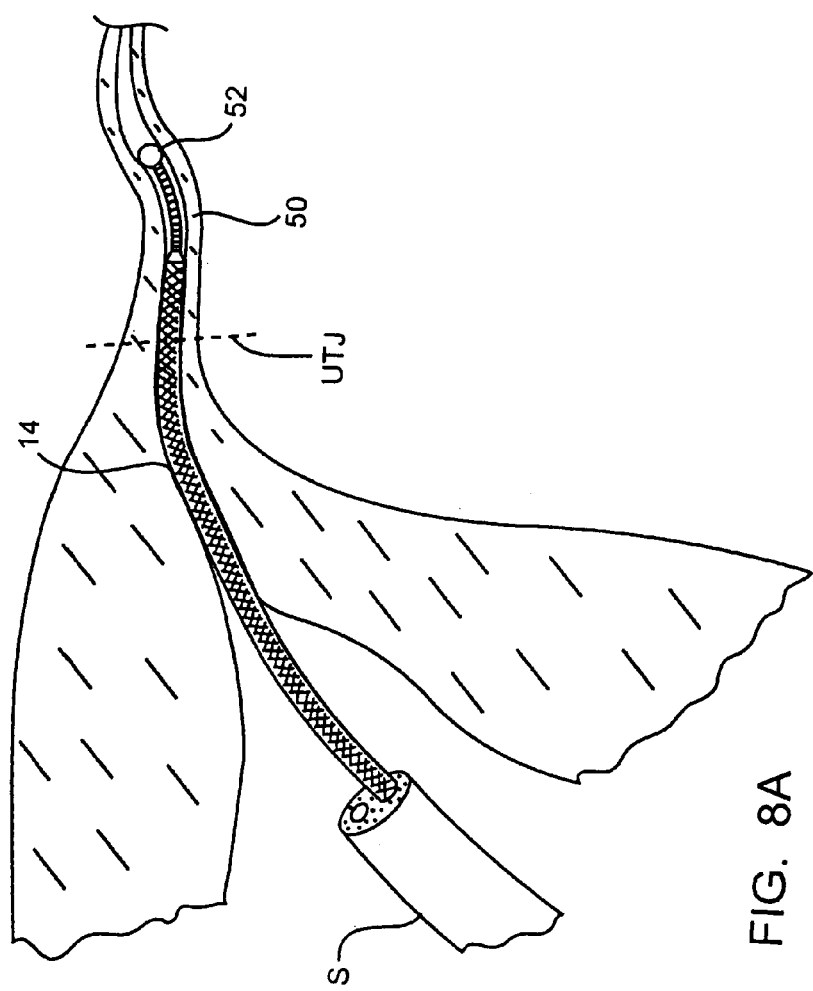
Figure 8B:
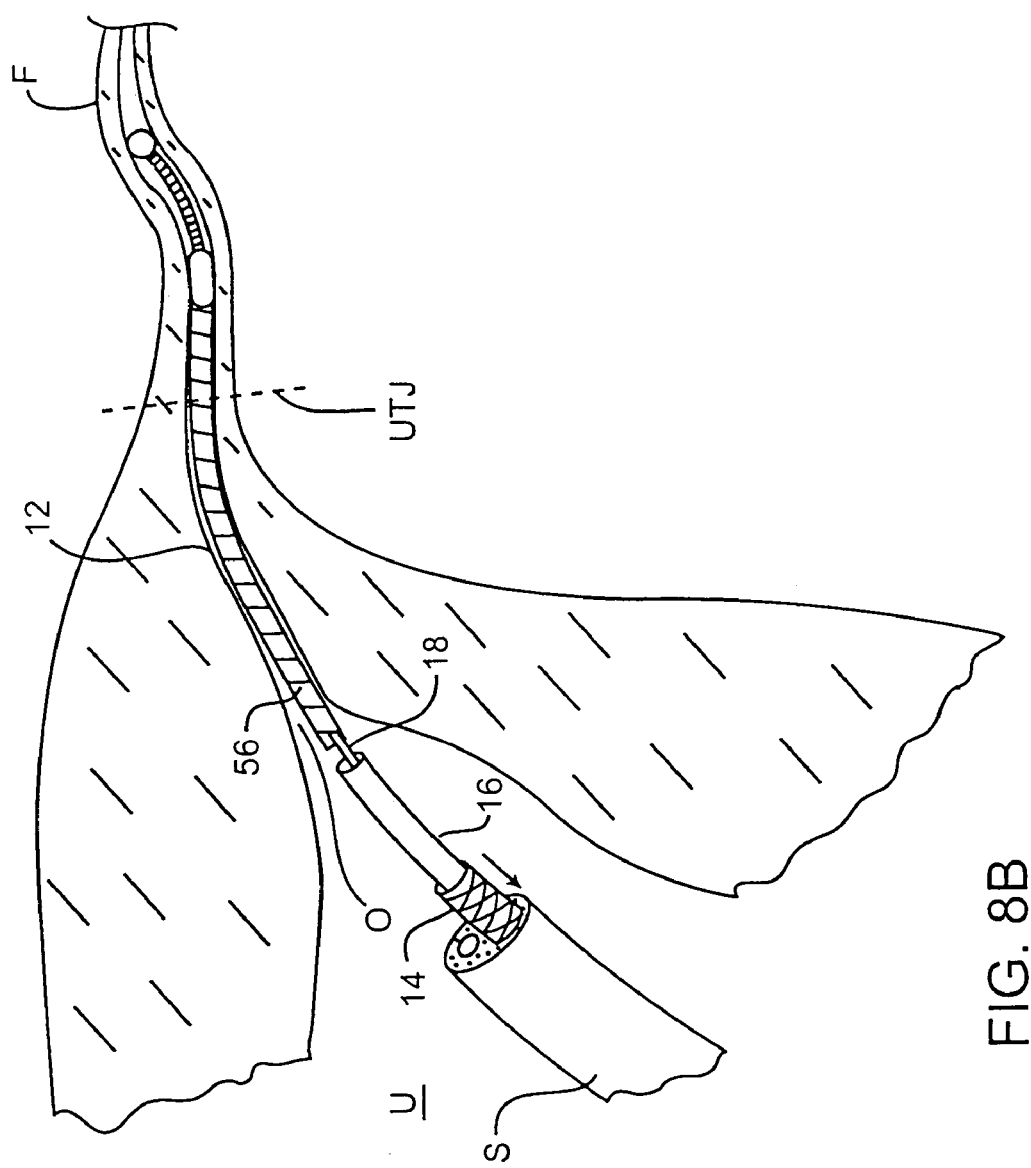
Figure 8C:
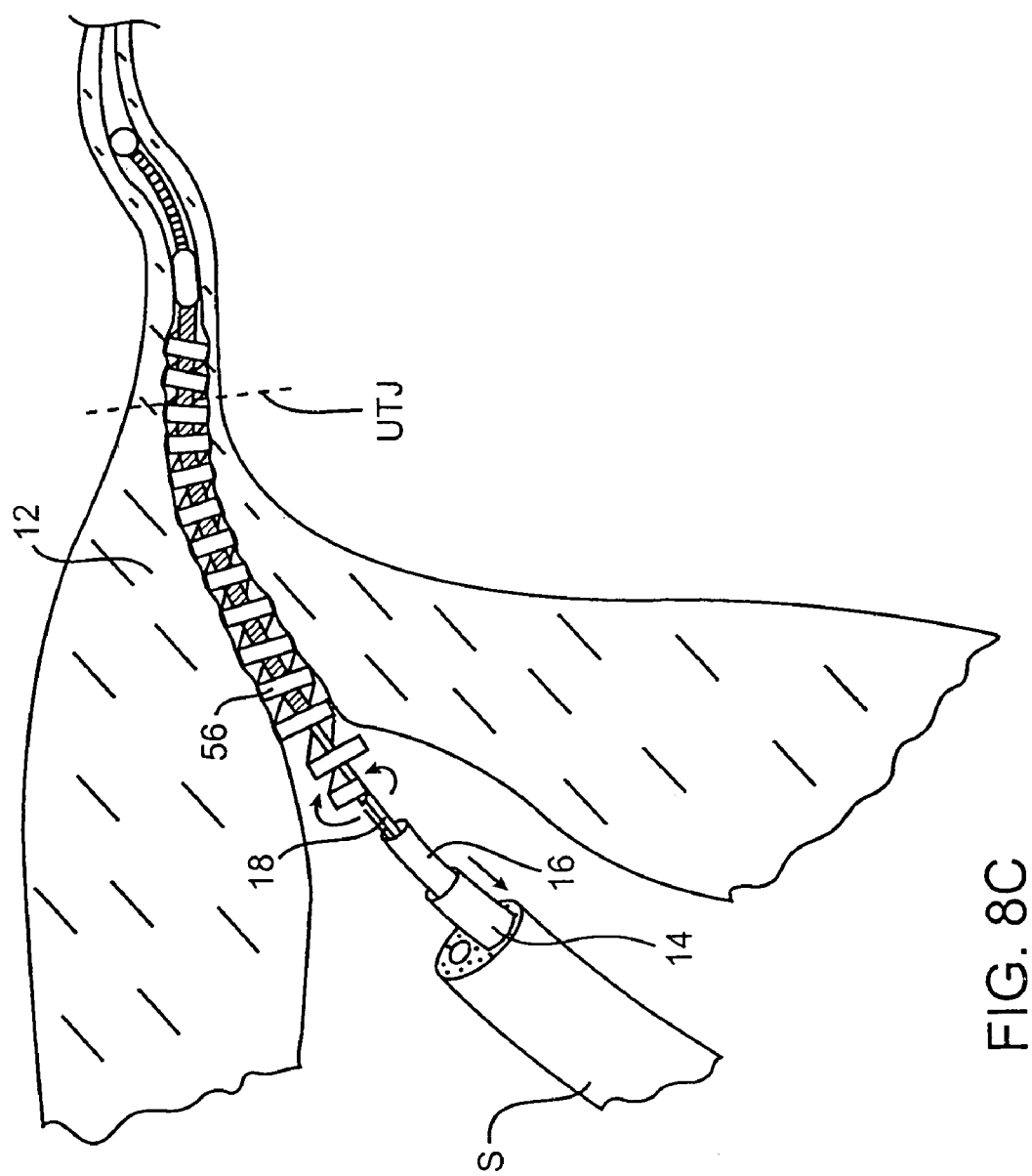
Figure 8D:
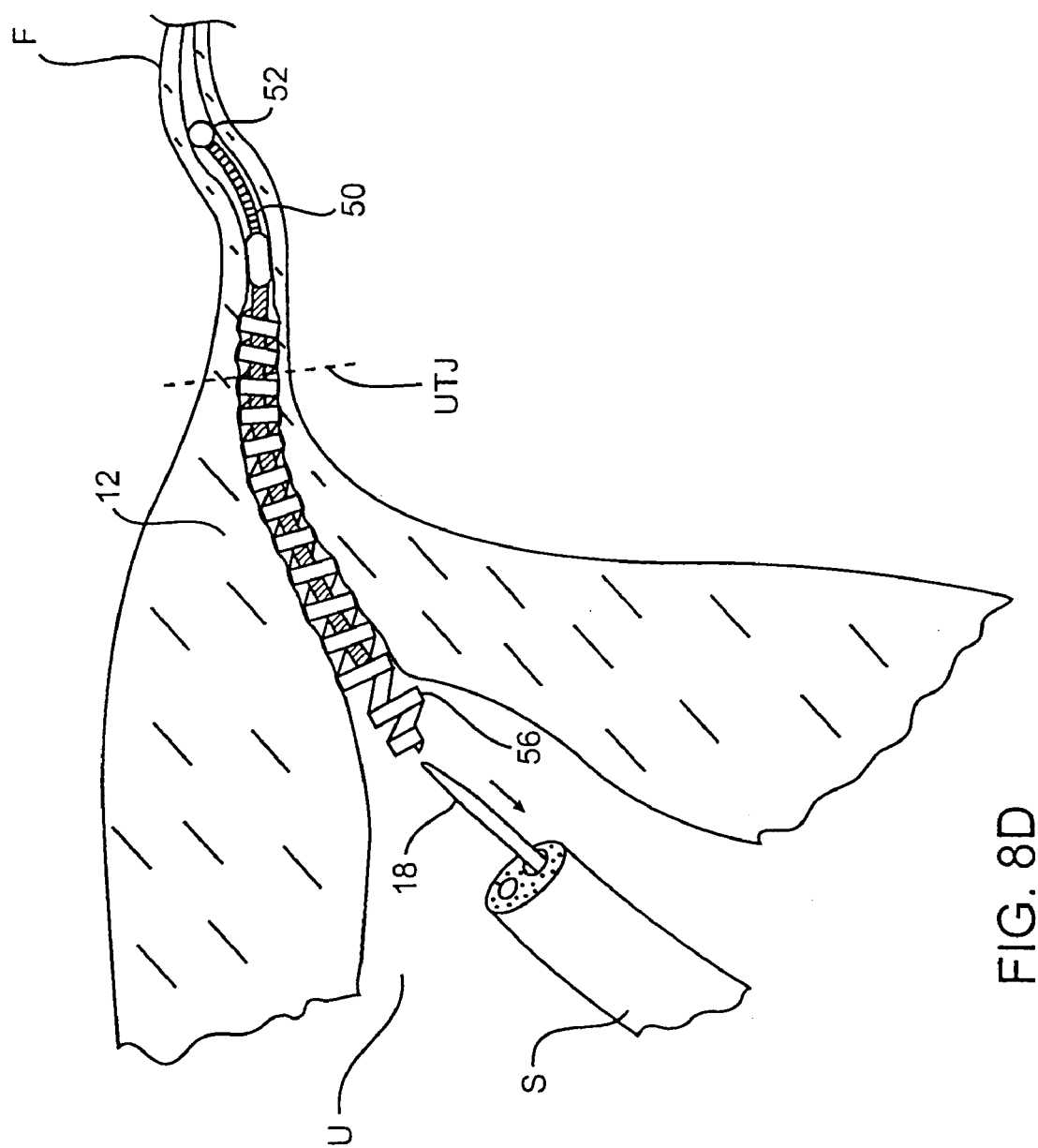

An exemplary method for use of contraceptive system 10 can be understood with reference to FIGS. 8 through 8D. System 10 is introduced transcervically through uterus U, generally under optical direction. Using hysteroscope S the physician directs the distal end of the system toward ostium O of fallopian tube F. Alternatively, some or all of the procedure may be performed under any medical imaging modality, including fluoroscopy, sonography, computer tomography, or the like. Uterus U may be irrigated using scope S and/or a separate irrigation system. Once ostium O is located and the scope S is oriented toward the ostium, system 10 is advanced distally through the working lumen of the scope and through the ostium and into the fallopian tube using distal portion 24 of the contraceptive device as a guidewire, while the remainder of the contraceptive device remains covered by sheath 14.

The outer hydrophilic coating of sheath 14 minimizes friction while advancing system 10, and the sheath also provides structural column strength to the system. The distal ball tip of distal portion 24 aids tracking and navigation through fallopian tube F, while the primary coil structure flexes laterally to track the tortuous bends often found within the fallopian tube. In the exemplary embodiment, core wire 18 extends into distal portion 24 to enhance column strength of the distal portion beyond sheath 14, but does not extend to the ball tip. Hence, the stiffness of distal portion 24 increases proximally, further enhancing the distal portion's ability to track the lumen.

In the exemplary embodiment, sheath 14 includes a visual marker 98 which can be seen from the scope of hysteroscope S (see FIG. 8B). Marker 98 will preferably be positioned partially within ostium O and partially within uterus U, thereby indicating that contraceptive device 12 is disposed at the target position, as the sheath, core shaft, and contraceptive device are releasably locked together during advancement and positioning. As described above, marker 98 may comprise a bumper, a structure which extends radially from the sheath to provide a tactile position indication.

Preferred positioning of contraceptive device 12 is illustrated in FIG. 8B. Preferably, device 12 extends along the uterotubal junction UTJ, with the device ideally extending both proximally and distally of the uterotubal junction. The uterotubal junction UTJ typically has a length in a range from about 1 to about 2 cm, and outer coil 56 will preferably extend proximally beyond ostium O into uterus U by a distance in a range from about 0.5 to about 1.0 cm. Outer coil 56 will preferably extend distally of the uterotubal junction UTJ by a distance of at least 0.6 cm. Ideally, outer coil 56 will extend both proximally and distally of the plane of the uterotubal junction UTJ by a distance of at least about 0.275 inches. Extending the expandable structure both distally and proximally of this effective isthmus can provide anchoring proximally and distally of the isthmus, thereby avoiding movement of contraceptive device 12 from the target position while tissue ingrowth takes place. Advantageously, positioning accuracy with a range of about 1 cm may be provided by limiting marker 98 to a 1 cm length. This provides a sufficient positional tolerance for ease of use while helping to ensure reliable, well-anchored deployments.

Referring now to FIGS. 8A, 8A1, and 8A2, positioned contraceptive device 12 is deployed by first withdrawing sheath 14 from over the expandable structure. Touhy-Borst valve 32 of proximal housing 30 is actuated to allow sliding movement between sheath 14 and release catheter 16, and the proximal housing slides proximally along the release catheter while maintaining fitting 36 of the release catheter in a fixed position, as illustrated in FIG. 8A2. Advantageously, core shaft 18 and release catheter 16 remain locked together by fitting 36, so that the expandable structure does not impede proximal movement of the sheath. Retraction of sheath 14 from the positioned (but as yet unexpanded) device 12 leaves the distal end of deployment system 10 in the configuration illustrated in FIG. 8B. Advantageously, it may still be possible to adjust the position of the device while viewing a proximal portion of outer coil 56.

As can be understood with reference to FIGS. 8B and 8B1, once proximal housing 30 engages fitting 36, the Touhy-Borst valve of the fitting can be actuated so as to allow movement between core shaft 18 and release catheter 16. The core shaft and/or release catheter may be allowed to rotate relative to each other to at least partially expand outer coil 56. The surgeon slides release catheter 16 proximally while holding handle 38 of core shaft 18 in a fixed position, as shown in FIG. 8B2, thereby disengaging the release catheter from the outer coil and allowing the outer coil to expand fully and firmly attaching contraceptive device 12 to the surrounding tissue, as seen in FIG. 8C.

Referring now to FIG. 8C1, to fully release contraceptive device 12 from the remaining components of delivery system 10, core shaft 18 is rotated to disengage the threaded coupling 42 between the core shaft and the contraceptive device. As described above, the direction of rotation of the core shaft for disengagement will be opposite that imposed by the wind-down torque, so that the wind-down torque helps maintain the threaded engagement prior to release of the core shaft relative to release catheter 16. Once core shaft 18 is unthreaded from contraceptive device 12, the core shaft and other delivery components can be withdrawn proximally into scope S, as shown in FIG. 8D. Scope S can view outer coil 56 to verify that the amount of the coil extending proximally of the ostium is within an acceptable range (and hence that device 12 is disposed at the target position) and the scope can be withdrawn after visually verifying that the deployment has been successful.

Figure 9:
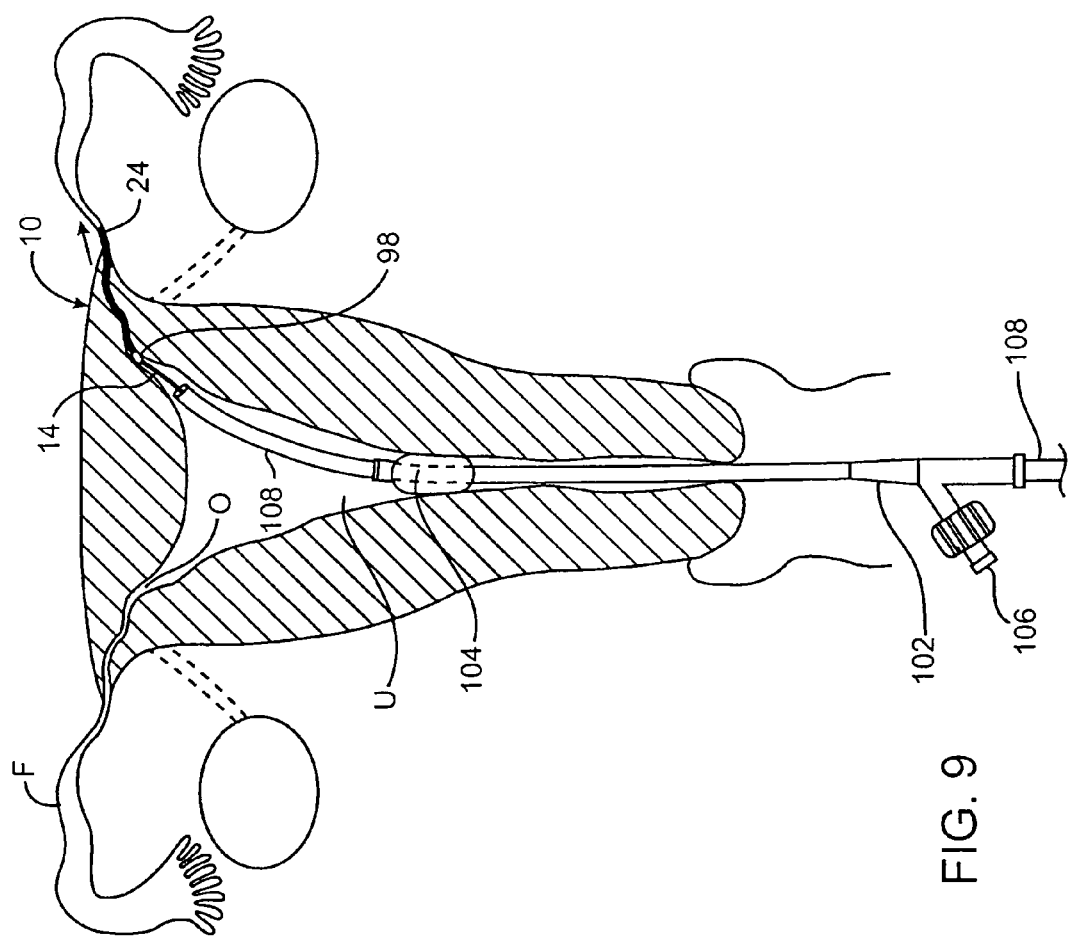
FIG. 9 illustrates an alternative deployment method using an alternative imaging system.

Referring now to FIG. 9, a variety of alternative deployment methods might be used to deploy the contraceptive system 10. For example, using a simple cervical catheter 102, deployment might be directed sonographically, fluoroscopically, under magnetic resonance imaging, and possibly even solely from tactile information. In the alternative exemplary method illustrated in FIG. 9, a balloon 104 of cervical catheter 102 is inflated via inflation port 106. This allows the uterus U to be distended by introduction of distention media through a uterine catheter 108 inserted through the working lumen of cervical catheter 102. Preferably, anatomy and target location identification, device positioning, deployment, detachment, and position confirmation (as outlined in method 2 with reference to FIG. 1A) is performed under the guidance of ultrasound and/or fluoroscopic imaging. Relevant uterine catheter manipulation structures and methods are described in U.S. Pat. Nos. 5,346,498; and 5,389,100, the full disclosure of which are incorporated herein by reference.

As described above, the delivery systems of the present invention will often hold the contraceptive device in a fixed position while the contraceptive device is uncovered, expanded, and/or released. When moving, for example, outer sheath 14 so as to expose the proximal portion of the contraceptive device, friction between the outer sheath and the surrounding hysteroscope (or other introducing structure, surrounding tissue, or the like) may cause inadvertent movement of the contraceptive device. To avoid such inadvertent movement, an outer sleeve may be slidably disposed around outer sheath 14. The sleeve provides a sliding interface between the sheath and surrounding structures. By axially coupling the sleeve and core shaft 18, friction between the sleeve and surrounding structures may inhibit movement of the contraceptive device. Such a sleeve will typically be shorter in length than sheath 14, and is more fully described in a concurrently filed application for a Deployment Actuation System for Intrafallopian Contraception, which has issued as U.S. Pat. No. 6,709,667, previously incorporated by reference.

Figure 10:
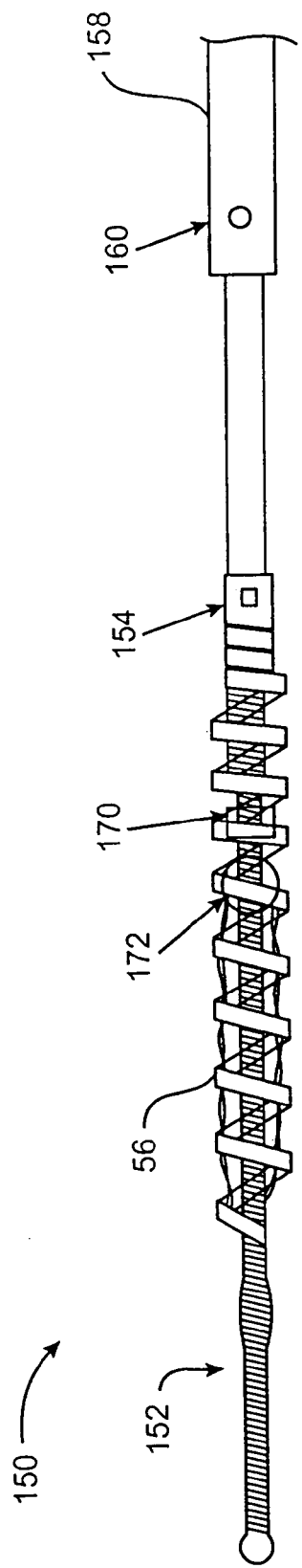
FIG. 10 schematically illustrates a side view of alternative distal components for a contraceptive system.
Figure 11A:
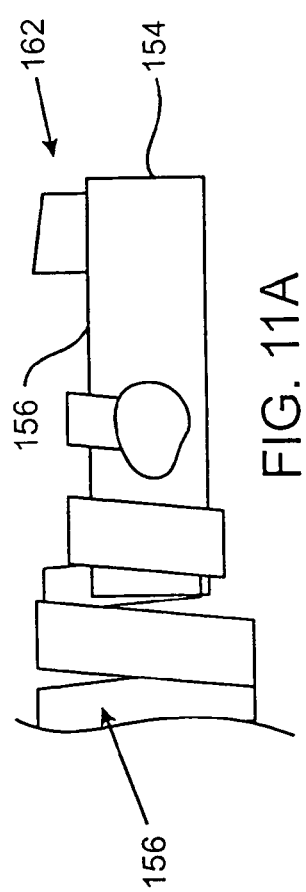
FIGS. 11A and 11B illustrate alternative coupling structures at a proximal end of an outer helical coil, the coil couplers adapted to releasably maintain torque on the coil in cooperation with a release catheter.

Referring now to FIGS. 10 and 11A, an alternative contraceptive system 150 includes a contraceptive device 152 having many of the components described above, but having an alternative wind-down outer coil connector 154 disposed at a proximal end of outer coil 56. An alternative release catheter 158 having a corresponding connector 160 for engagement with connector 154 of contraceptive device 152 again allows a wind-down torque to be released, as described above. In this embodiment, wind-down connector 160 of release catheter 158 comprises an opening which receives a protrusion 162 extending radially from a tubular band 156 of connector 154. In the exemplary embodiment, band 156 comprises a platinum tube having a length of about 2.2 mm, and is affixed to coil 56 using a solder bond. Protrusion 162 also comprises solder.

Figure 11B:
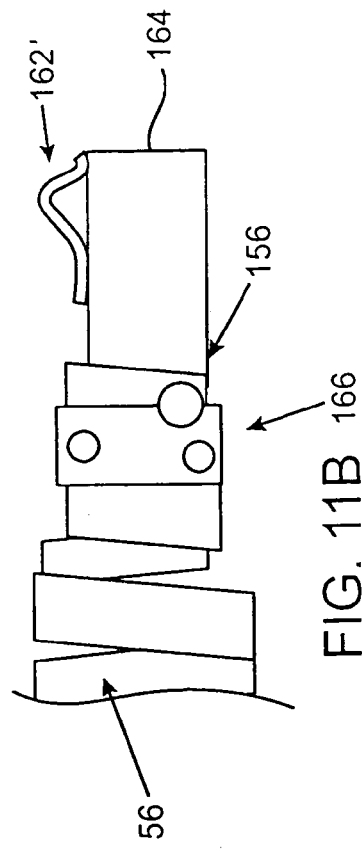

Referring now to FIG. 11B, an alternative wind-down connector 164 may be affixed to a proximal end of outer coil 56 using a stainless steel ring 166, with the outer coil welded to band 156 and the stainless steel ring welded to the band over the outer coil. In this embodiment, protrusion 162' is formed by welding a bent platinum ribbon to band 156. Band 156 may have a length of about 1.6 mm and an outer diameter of about 0.031", while protrusion 162' has an axial length of about 0.020", and is formed of a ribbon having a thickness of about 0.0015", with the ribbon being bent so as to extend about 0.04" radially beyond band 156. Typically, protrusions 162, 162' will extend radially a sufficient distance to extend into opening 160 of release catheter 158, with the release catheter and/or protrusion often having sufficient flexibility to allow disengagement of the wind-down connectors.

Figure 12:
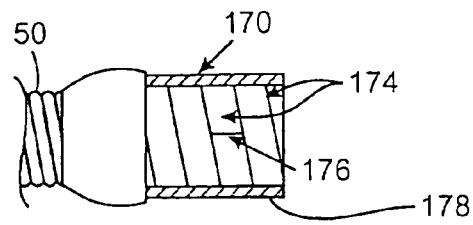
FIG. 12 is a partial cut-away view of a proximal end of a primary coil showing an alternative threaded connector for coupling the primary coil to a core wire.
Figure 13:
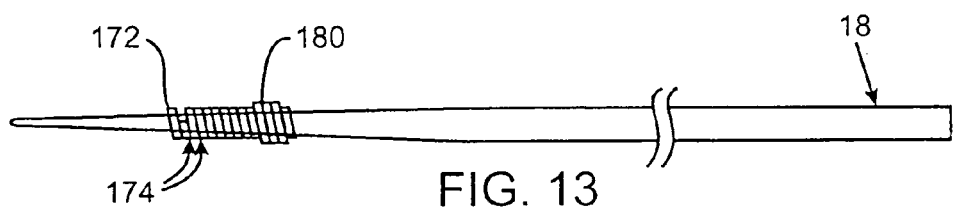
FIG. 13 is a schematic illustration of an alternative core wire structure having a threaded connector suitable for engagement with the primary coil connector of FIG. 12.

Referring now to FIGS. 10, 12, and 13, contraceptive system 150 also uses alternative threaded connectors 170, 172 for engagement between primary coil 50 and core wire 18. Threaded connector 170 is affixed to primary coil 50 of contraceptive device 152 by solder, and includes first and second interleaved coils 174, with one of the interleaved coils terminating ¼ turn distally of the other to define a ¼ open-winding or thread 176. An outer tube or stopper band 178 inhibits radial displacement of the threads, particularly when the threads are engaged between core wire 18 and the stopper. Preferably, primary coil 50 comprises 0.005" diameter 316L stainless steel wound to have an outer diameter of 0.0125" with a 0.005" pitch and a length of about 2.9 cm. First and second interleaved coils 174 comprise 0.0039"×0.008" 316L stainless steel ribbon wound to have an outer diameter of about 0.0205" and a 0.018" pitch. Stopper 178 may comprise a platinum or PtIr band having an outer diameter of about 0.026" and a length of about 1 mm. The stopper 178 and/or other components of at least one of the connectors coupling inner coil 50 to corewire 18 and outer coil 56 to a deployment catheter will preferably provide a high contrast imaging marker.

Threaded connector 172 may similarly comprise interleaved coils 174 having differing lengths or axially positions so as to provide a ¼ turn open winding or thread, with the interleaved coils typically having more windings than used on threaded connector 170. An additional blocker coil 180 is disposed over and/or proximally of interleaved coils 174, with the coil being soldered to core wire 18, typically using a SnAg solder.

Preferably, threaded connectors 170, 172 will have less than five windings engagement therebetween, more preferably having less than two engaged windings and ideally having less than a single winding of engagement. These limited engaged windings are sufficient to maintain coupling between core wire 18 and the contraceptive device so long as wind-down torque is maintained, and facilitate detachment after release of the wind-down torque by limiting the number of rotations of core wire 18, friction between the core wire and the contraceptive device, and the like.

Figure 14:
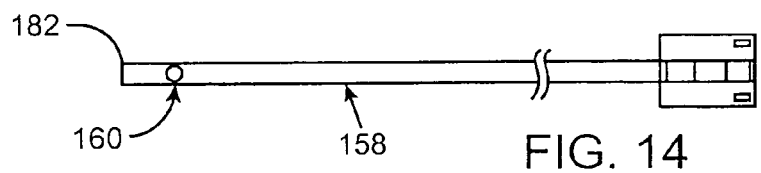
FIG. 14 schematically illustrates a release catheter suitable for releasably maintaining torque in cooperation with the connectors of FIGS. 11A and 11B.

Release catheter 158 is shown in isolation in FIG. 14. The specific configuration of connector or opening 160 may vary, for example, with the opening being nearer a distal end 182 of release catheter 14 when alternative protrusion 162' is used (rather than protrusion 162 formed of solder). Still further variations are possible, including rectangular openings or channels having differing shapes or extending axially to distal end 182. In general, coupler or opening 160 will have a circumferentially oriented surface to releasably maintain a wind-down torque by corresponding engagement with an associated connector of the contraceptive device. In the exemplary embodiment, release catheter 158 comprises an polyimide affixed to a proximal release catheter housing by an adhesive such as a Lock-Tite™ 3321 adhesive. During assembly, core wire 18 may be inserted through release catheter 158 and coupled to the contraceptive device with the outer coil 56 being wound-down over the primary coil, and the wind-down torque maintained by coupling the proximal portions of the core wire 18 and release catheter.

Figure 15:
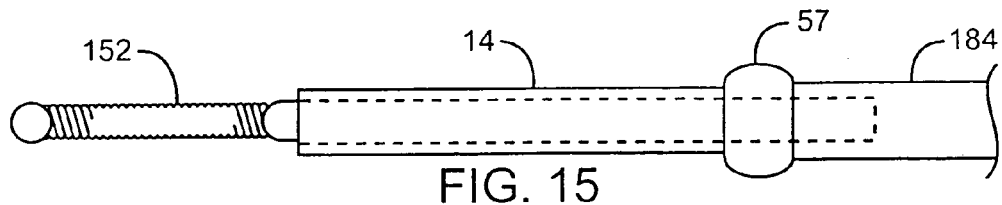
FIG. 15 schematically illustrates a separate positioning catheter slidably disposed over the sheath for axially positioning the contraceptive device.
Figure 18:
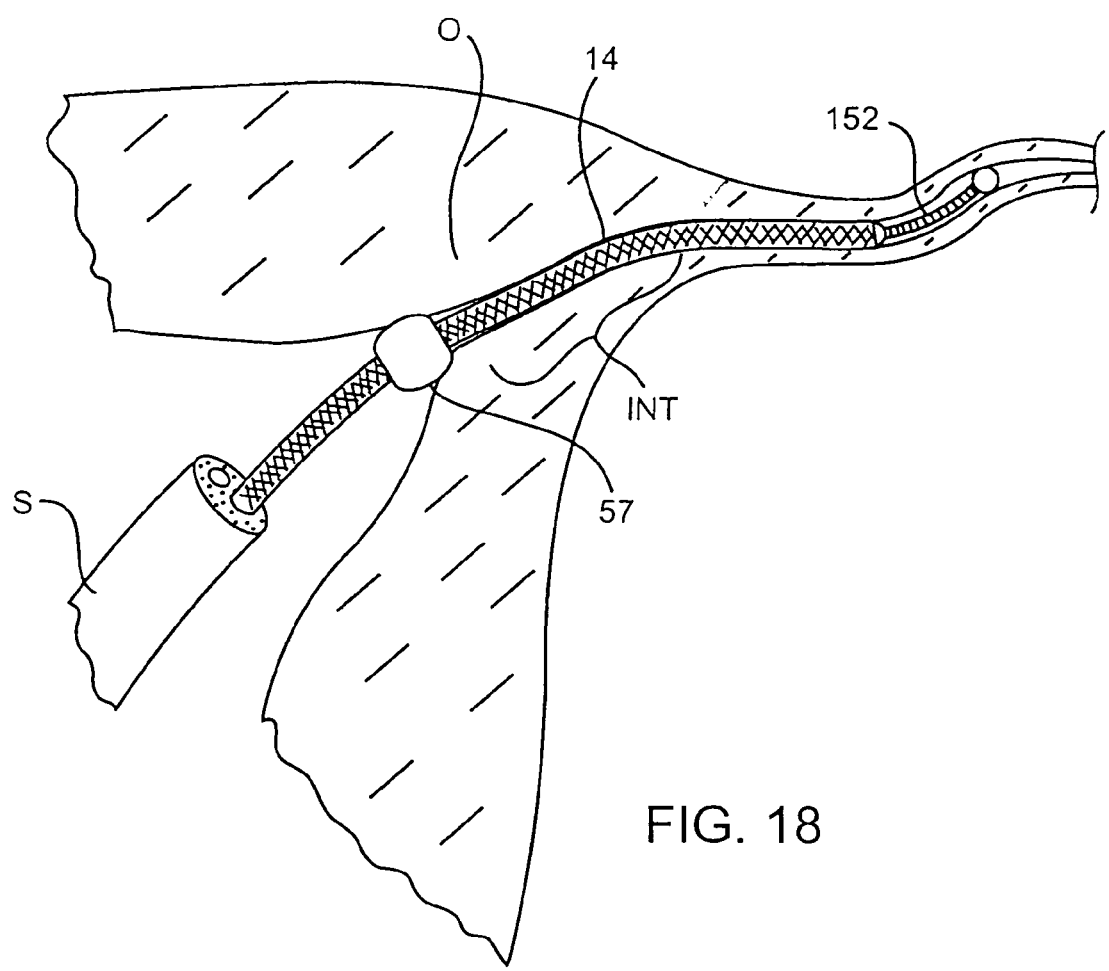
FIG. 18 illustrates a method for using a positioning surface of a sheath or positioning catheter.

Referring now to FIGS. 15 and 18, positioning surface 57 may optionally be affixed to sheath 14 to help axially position contraceptive device 152 across intermural region INT, as described above. Engagement between radially protruding positioning surface 57 and the uterine tissues surrounding ostium O allows initial axial positioning by taking advantage of the axially coupling of sheath 14 to contraceptive device 152. However, sheath 14 will be withdrawn proximally into scope S early-on during deployment, and it is often desirable to maintain the axially positioning of the contraceptive device at least until proximal coil 56 begins to expand radially.

As schematically illustrated in FIG. 15, by affixing positioning surface 57 (which may optionally comprise any of the alternative positioning surface configurations described hereinabove, or still further alternative structures such as radially expandable torroidal balloons, or the like) at a distal end of a separate positioning catheter 184 slidably disposed over sheath 14, the axial positioning provided by the positioning surface may be maintained during and/or after withdrawal of sheath 14. Optionally, a proximal portion of release catheter 184 may be axially coupled to a proximal portion of release catheter 16, core wire 18, or another of the axially elongate structures so as to maintain an axial position of contraceptive device 152 using positioning surface 57. Alternatively, the positioning surface may be movable independently of these structures.

Figure 16A:
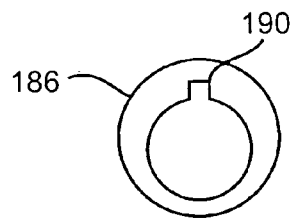
FIGS. 16A and 16B are end views of alternative embodiments of an integrated release catheter/sheath for both maintaining a wind-down torque on, and being slidably disposed over, an expandable outer coil.
Figure 16B:
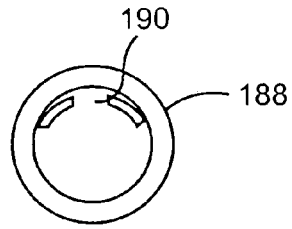
Figure 17:
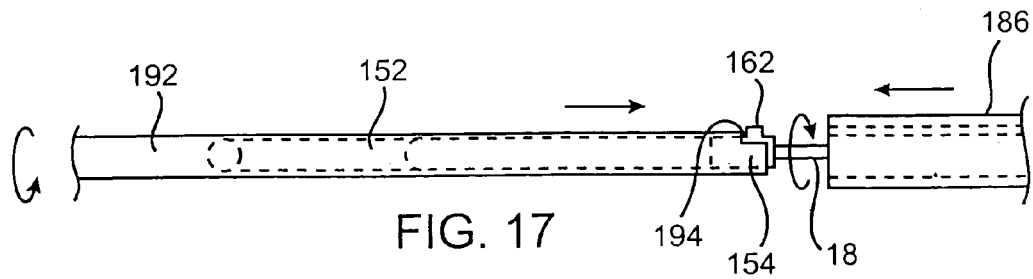
FIG. 17 schematically illustrates a tool and method for loading a radially expandable contraceptive device into a combination release catheter/sheath.

Still further structures and methods for releasably restraining the proximal, radially expandable portion of the contraceptive device might be provided, as can be understood with reference to FIGS. 16A, 16B, and 17. FIGS. 16A and 16B each illustrate a distal end of an integrated sheath/release catheter 186, 188 having an axially channel 190 defining a circumferentially oriented channel surface. Channel 190 cooperates with a protrusion 162 of connector 154 so as maintain wind-down torque on the radially expandable proximal coil of contraceptive device 152 via cooperation between core wire 18 and the integrated release catheter/sheath. Additionally, the integrated release catheter/sheath slidingly surrounds the proximal, radially expandable portion of contraceptive device 152 so as to facilitate insertion of the device into the fallopian tube. As illustrated in FIG. 17, a tubular tool 192 having a lumen (which receives the contraceptive device) and a notch 194 (which receives protrusion 162) may facilitate winding-down proximal coil 56 and insertion of the proximal coil into the integrated release catheter/sheath, particularly if the tool has an outer diameter sufficiently to allow introduction of the tool into the lumen over the contraceptive device.

Channel 190 will generally have a length sufficient so as to allow an integrated release catheter/sheath to slide axially from over protrusion 162 and over the outer coil 56, typically having a length of about 2.5 cms. Channel 190 may be formed during fabrication of the tubular sheath structure as shown in FIG. 16A, or may be defined by structures (such as a stainless steel, or NiTi ribbon) affixed within the lumen using an adhesive, a supporting coil, and/or the like.

Figure 19:
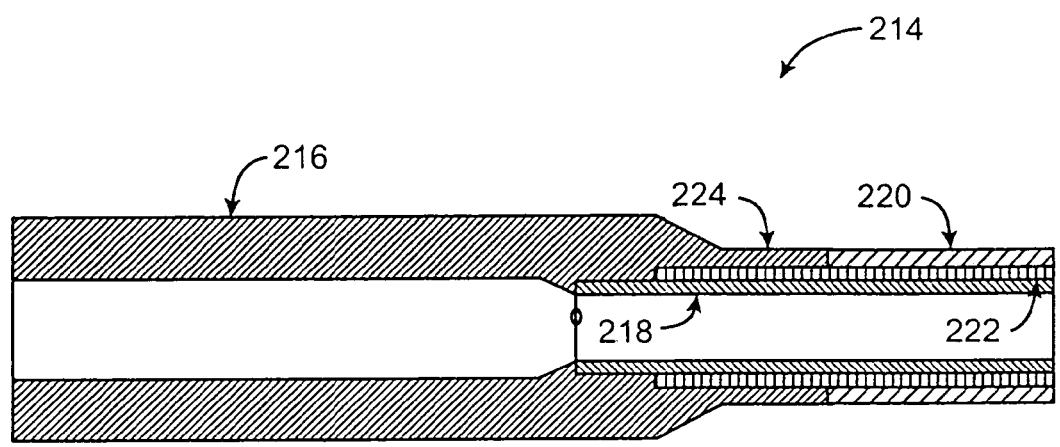
FIG. 19 illustrates an alternative outer sheath structure.

Referring now to FIG. 19, an alternative outer sheath 214 may be used in place of outer sheath 14 in the system of FIG. 1B. Sheath 214 has a proximal portion 216 with a relatively stiff, thicker-walled tubular structure, such as a PeBax® polymer tube having an outer diameter of about 0.062", and an inner diameter of about 0.042". A distal portion of sheath 14 includes an inner tube 218 of a low friction polymer and an outer tube 220 of a polymer, (such as carbothane® 73A) with at least one ribbon coil 222 therebetween. Inner tube 218 may comprise a PTFE (such as a Teflon™ material) with an inner diameter of about 0.034" and a wall thickness of about 0.001" with the outer diameter etched, and a length of about 5.0 cm, while there are preferably two counterwound ribbon coils 222 of a superelastic or shape memory alloy, such as nickel titanium (optionally with chromium) of about 0.007" by about 0.010" with a pitch of about 0.015" and a length of about 4.0 cm. Inner tube 218 might alternatively comprise ETFE, gamma stable PTFE, FEP, or the like, while ribbon coils 222 may comprise a stainless steel or other medical grade materials. An inner diameter of the distal portion may be about 0.034", with the distal outer diameter of sheath 214 being about 0.041". An intermediate outer tube 224 may comprise a polyurethane having a durometer of about 55. A length of outer tube 220 may be about 1.0 cm, a length of intermediate tube 224 may be about 5 mm, and a length of proximal portion 216 may be about 40 cm.

Figure 20:
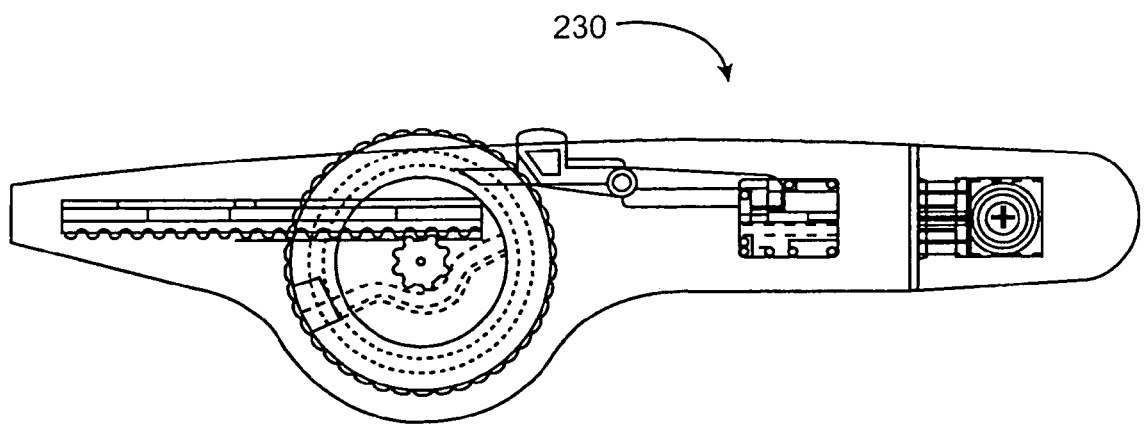
FIG. 20 schematically illustrates an optional proximal handle to facilitate coordinated movement of the structures of the delivery system.

As can be understood with reference to FIG. 20, and as explained in detail in co-pending application Ser. No. 09/644,287, which has issued as U.S. Pat. No. 6,709,667, a proximal handle mechanism 230 may be provided to help coordinate motion of the outer sheath, delivery catheter, corewire, and/or the like. This proximal handle may have a handle body which is axially coupled to the contraceptive device, and any of a wide variety of actuation mechanisms (such as syringe-like sliders, ratcheting trigger handles, rack-and-pinion thumb wheels, and the like) can be used to move, for example, a proximal end of the outer sheath 14 and/or a proximal end of release catheter 16 relative to a proximal end of core wire 18. Advantageously, these proximal handle mechanisms can be arranged to, for example, expose the proximal portion of contraceptive device 12, then deploy the retention structure, and then detach the deployed device from the delivery system (as explained above), with two or more of these steps integrated into a continuous actuation movement at handle 230. Such actuation handles may greatly reduce the workload on the attending medical staff, possibly reducing the number of persons needed to effect deployment, and/or allowing contraceptive device exposure, deployment, and/or detachment to be effected with one hand on handle 230 (allowing the other hand to position a hysteroscope or the like).

Still further modifications of the contraceptive device and/or delivery system are possible. For example, polyester fibers may be disposed both within primary coil 50 (ideally in the form of fiber loops) and around coil 50 (ideally in the form of wound Dacron® layers disposed between primary coil 50 and outer coil 56) so as to more fully occlude the tubal lumen.

While the exemplary embodiment of the present invention has been described in some detail, for clarity of understanding and by way of example, a variety of adaptations, changes, and modifications will be obvious to those who are skilled in the art. Hence, the scope of the present invention is limited solely by the following claims.

What is claimed is:

1. A contraceptive method comprising:
   guiding a contraceptive device distally into an ostium of a fallopian tube wherein a sheath covers the contraceptive device;
   avoiding perforation of the fallopian tube and facilitating tubal navigation of the fallopian tube with a distal ball tip of a distal portion of the contraceptive device, the ball tip having a diameter in a range from about 0.020 to about 0.050 inches;
   uncovering the contraceptive device by withdrawing the sheath from the contraceptive device; and
   releasing the uncovered contraceptive device so that the contraceptive device inhibits conception permanently.

2. The method of claim 1, wherein the contraceptive device comprises an axially elongate flexible structure, and further comprising supporting an axially elongate flexible structure with the surrounding sheath during the guiding.

3. The method of claim 2, further comprising supporting at least a portion of the axially elongate flexible structure with a core support disposed within an axially oriented lumen of the axially elongate flexible structure during the guiding.

4. The method of claim 3, further comprising removing the core support during the releasing.

5. The method of claim 1, further comprising maneuvering the contraceptive device into the ostium while the contraceptive device flexes laterally to track through the uterotubal junction.

6. The method of claim 1, further comprising positioning the contraceptive device across the muscular isthmus of the uterotubal junction.

7. A contraceptive method comprising:
   inserting a contraceptive device distally into an ostium of a fallopian tube;
   uncovering the inserted contraceptive device by withdrawing a sheath from around the contraceptive device;
   maintaining an expandable structure of the contraceptive device in a small profile configuration during the uncovering so as to avoid restricting movement of the sheath during the withdrawing;
   radially expanding the uncovered expandable structure to a large profile configuration so as to affix the contraceptive device within the ostium; and
   releasing the uncovered contraceptive device so that the contraceptive device inhibits contraception.

8. The contraceptive method of claim 7, wherein the expandable structure is maintained in the small profile configuration by sustaining a restraint on the expandable structure between a first elongate body extending from a proximal handle to the expandable structure and a second elongate body extending from the proximal handle to the contraceptive device, whereby the restraint is releasable so as to expand the exposed expandable structure from the proximal handle.

9. The contraceptive method of claim 8, wherein the first and second elongate bodies sustain a wind-down torque on the expandable structure, the radially expanding comprising actuating the proximal handle so as to release a proximal end of the expandable structure relative to a distal end of the expandable structure, and so that the expandable portion unwinds and expands.

10. A contraceptive method comprising:
    guiding a contraceptive device distally into an ostium of a fallopian tube of a patient body wherein a sheath supports the contraceptive device, the contraceptive device comprising an elongate flexible structure;
    uncovering the contraceptive device by withdrawing the sheath while maintaining an expandable structure of the proximal portion in a small profile configuration with a wind-down torque between first and second elongate bodies so as to avoid restricting movement of the sheath;
    radially expanding the uncovered expandable structure to a large profile configuration so as to affix the contraceptive device within the ostium by actuating a proximal handle disposed outside the patient body, the proximal handle coupling proximal ends of the elongate bodies, so that the expandable portion unwinds and expands; and
    releasing the uncovered contraceptive device so that the contraceptive device inhibits conception by rotating the first elongate body in a direction opposite the direction of the wind-down torque to decouple the first elongate body from the contraceptive device, and by removing a core support extending into an axial lumen of the contraceptive device.

11. The contraceptive method of claim 10, wherein the wind-down torque twists the first elongate body in a first direction, and wherein the releasing comprises rotating the first elongate body in a second direction opposite the first direction to decouple the first elongate body from the contraceptive device.

* * * * *